United States Patent [19]

Bruneau et al.

[11] Patent Number: 5,173,496

[45] Date of Patent: Dec. 22, 1992

[54] THERAPEUTIC PREPARATIONS CONTAINING INDAZOLE DERIVATIVES

[75] Inventors: Pierre A. R. Bruneau, Ludes, France; Frank Carey, Wilmslow, England; Christian R. E. Delvare, Reims, France; Keith H. Gibson; Rodger M. McMillan, both of Macclesfield, England

[73] Assignees: ICI Pharma, Cergy Cedex, France; Imperial Chemical Industries PLC, London, England

[21] Appl. No.: 863,333

[22] Filed: Apr. 2, 1992

Related U.S. Application Data

[63] Continuation of Ser. No. 532,348, Jun. 5, 1990, abandoned, which is a continuation of Ser. No. 143,373, Jan. 13, 1988, abandoned.

[30] Foreign Application Priority Data

Jan. 19, 1987 [EP] European Pat. Off. ........ 87400122.5
Jul. 31, 1987 [EP] European Pat. Off. ........ 87401798.1

[51] Int. Cl.$^5$ .................... A61K 31/44; A61K 31/415
[52] U.S. Cl. ..................................... 514/338; 514/365; 514/394; 514/405; 514/438; 514/459
[58] Field of Search ............... 514/338, 365, 438, 394, 514/459, 405

[56] References Cited

FOREIGN PATENT DOCUMENTS 0072961 3/1983 European Pat. Off. .
0208874 1/1987 European Pat. Off. .
47-29900 4/1947 Japan .

OTHER PUBLICATIONS

J. Chem. Soc., 1921, 1053 Chem. Abs., 68, 13157k (1968).
Chem. Abs., 74, 53783s (1971).
Chem. Abs., 87, 68227f (1977).
Helv. Chim. Acta, 61 2264 (Chem. Abs. 89, 215535b) (1978).
Chem. Abs., 28, 5445 (1934).
Chem. Abs., 55, 5510e (1959).
J. Amer. Chem. Soc., 90, 313 (1968).
J. Organic Chem., 47, 4226 (1982).
J. Chem. Soc. Perkin I, 1972-2498 Chem. Abs., 87 200523 (1977).
Tet. Lett., 1979, 4765 Chem. Abs., 29, 3316 & 3317 (1935).
J. Chem. Soc., 1959, 2280 Patent Abstracts of Japan vol. 11, No. 124 (C-416) (2571) Apr. 17, 1987.
J. Heterocyclic Chemistry 1970, 7, 815-820.
J. Medicinal Chemistry 1984, 27, 768-772.

Primary Examiner—Leonard Schenkman
Attorney, Agent, or Firm—Cushman, Darby & Cushman

[57] ABSTRACT

The invention concerns pharmaceutical compositions containing a 1,2-dihydro-3H-indazol-3-one derivative of the formula I

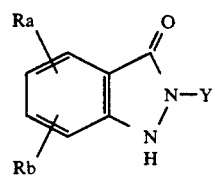

wherein Ra is hydrogen, halogeno, nitro, hydroxy, (2-6C)alkanoyloxy, (1-6C)alkyl, (1-6C)alkoxy, fluoro-(1-4C)alkyl, (2-6C)alkanoyl, amino, (1-6C)alkylamino, di-[(1-4C)alkyl]amino, (2-6C)alkanoylamino or hydroxy-(1-6C)alkyl; Rb is hydrogen, halogeno, (1-6C)alkyl or (1-6C)alkoxy; and Y is a group of the formula —A$^1$—X—A$^2$—Q in which A$^1$ is (1-6C)alkylene, (3-6C)alkenylene, (3-6C)alkynylene or cyclo(3-6C)alkylene, or A$^1$ is phenylene; X is oxy, thio, sulphinyl, sulphonyl, imino, (1-6C)alkylimino, (1-6C)alkanoylimino, iminocarbonyl or phenylene, or X is a direct link to A$^2$; A$^2$ is (1-6C)alkylene, (3-6C)alkenylene or (3-6C)alkynylene or A$^2$ is cyclo(3-6C)alkylene or is a direct link to Q, or the group —A$^1$—X—A$^2$— is a direct link to Q; or Y is (2-10C)alkyl, (3-10C)alkenyl or (3-6C)alkynyl; and Q is aryl or heteroaryl.

The invention also provides novel 1,2-dihydro-3H-indazol-3-ones, processes for their production and the use of 1,2-dihydro-3H-indazol-3-ones for the manufacture of medicaments for the treatment of various allergic and inflammatory diseases.

7 Claims, No Drawings

THERAPEUTIC PREPARATIONS CONTAINING INDAZOLE DERIVATIVES

This is a continuation of application Ser. No. 07/532,348, filed on Jun. 5, 1990, which was abandoned upon the filing hereof, which is an FWC of 07/143,373, filed Jan. 13, 1988, abandoned.

This invention concerns novel therapeutic preparations and more particularly novel compositions containing an indazole derivative which is an inhibitor of the enzyme 5-lipoxygenase (hereinafter referred to as 5-LO). The invention also concerns certain novel indazole derivatives and processes for their manufacture. Also included in the invention is a novel use of indazole derivatives in the treatment of various inflammatory and/or allergic diseases in which the direct or indirect products of 5-LO catalysed oxidation of arachidonic acid are involved, and in the production of new medicaments for such use.

As stated above the indazole derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered (and this is the basis for the present invention) that certain indazole derivatives are effective as inhibitors of the enzyme 5-LO and thus of leukotriene biosynthesis. Thus, such compounds are of value as therapeutic agents in the treatment of, for example, allergic conditions, asthma, cardiovascular and cerebrovascular disorders, and inflammatory and arthritic conditions, mediated alone or in part by one or more leukotrienes.

According to the invention there is provided a pharmaceutical composition which comprises as active ingredient a 1,2-dihydro-3H-indazol-3-one (hereinafter abbreviated to "indazolone") derivative of the formula I (set out hereinafter) wherein Ra is hydrogen, halogeno, nitro, hydroxy, (2-6C)alkanoyloxy, (1-6C)alkyl, (1-6C)alkoxy, fluoro-(1-4C)alkyl, (2-6C)alkanoyl, amino, (1-6C)alkylamino, di-[(1-4C)alkyl]amino, (2-6C)alkanoylamino or hydroxy-(1-6C)alkyl; Rb is hydrogen, halogeno, (1-6C)alkyl or (1-6C)alkoxy; and Y is a group of the formula $-A^1-X-A^2-Q$ in which $A^1$ is (1-6C)alkylene, (3-6C)alkenylene, (3-6C)alkynylene or cyclo(3-6C)alkylene optionally bearing a substituent selected from hydroxy, cyano, carbamoyl, carboxy, (1-4C)alkoxycarbonyl and phenyl, or $A^1$ is phenylene optionally bearing a substituent selected from halogeno, trifluoromethyl, (1-6C)alkyl or (1-6C)alkoxy; X is oxy, thio, sulphinyl, sulphonyl, imino, (1-6C)alkylimino, (1-6C)-alkanoylimino, iminocarbonyl (that is —NH-.CO— or —CO.NH—) or phenylene optionally bearing a substituent selected from halogeno, trifluoromethyl, (1-6C)alkyl or (1-6C)alkoxy, or X is a direct link to $A^2$; $A^2$ is (1-6C)alkylene, (3-6C)alkenylene or (3-6C)alkynylene in which one constituent methylene group may be replaced by an oxy or thio group, or $A^2$ is cyclo(3-6C)alkylene as defined above or is a direct link to Q, or the group $-A^1-X-A^2-$ is a direct link to Q; or Y is (2-10C)alkyl, (3-10C)alkenyl or (3-6C)alkynyl optionally bearing a substituent selected from (1-6C)alkoxy, (1-6C)alkylthio, (1-6C)alkylsulphinyl, (1-6C)alkylsulphonyl, cyano, carbamoyl, N-[(1-6C)alkyl]carbamoyl, N,N-di-[(1-4C)alkyl]carbamoyl, amino, (1-6C)alkylamino, di-[(1-4C)alkyl]amino, morpholino, piperidino, thiophenoxy and phenoxy; and Q is aryl, heteroaryl or a hydrogenated derivative thereof, which may optionally bear one or two substituents selected from (1-10C)alkyl, (2-10C)alkenyl, (1-10C)alkoxy, halogeno, nitro, hydroxy, oxo, (1-6C)ALKYLTHIO, (1-6C)alkylsulphinyl, (1-6C)alkylsulphonyl, amino, (1-6C)alkylamino, di-[(1-4C)alkyl]amino, carbamoyl, N-[(1-6C)alkyl]carbamoyl, N,N-di-[(1-4C)alkyl]carbamoyl, cyano, (1-4C)alkoxycarbonyl, carboxy, phenyl, phenyl-(1-4C)alkyl, fluoro-(1-4C)alkyl, (2-6C)alkanoyl, (2-6C)alkanoylamino, di-[(2-6C)alkanoyl]amino and hydroxy-(1-6C)alkyl, or may bear a (1-4C)alkylenedioxy substituent; and wherein any one or more of said phenyl, phenoxy or thiophenoxy substituents may themselves optionally bear one or two optional substituents selected from halogeno, fluoro-(1-4C)alkyl, nitro, carbamoyl, N-[(1-6C)alkyl]carbamoyl, N,N-di[(1-4C)alkyl]carbamoyl, cyano, (1-6C)alkyl and (1-6C)alkoxy substituents; provided that when Y is butyl or 4-methyl-, 4-methoxy- or 4-ethoxyphenyl, Ra is other than hydrogen, chloro, methyl or ethyl; and when Y is a straight chain (2-5C)alkyl optionally bearing a terminally situated hydroxy substituent, or is unsubstituted phenyl or benzyl, or is benzyl bearing an acetyl substituent, Ra is other than hydrogen;

or a pharmaceutically acceptable salt thereof; or a (1-4C)alkoxycarbonyl derivative thereof; said active ingredient together with a pharmaceutically acceptable diluent or carrier.

The chemical formulae referred to herein by Roman numerals are set out for convenience on a separate sheet hereinafter. In this specification the term "alkyl" includes both straight and branched alkyl groups but references to individual alkyl groups such as "propyl" are specific for the straight chain ("normal") version only, any branched chain isomer such as "isopropyl" being referred to specifically. An analogous convention applies to other generic terms.

It is to be understood that, insofar as certain of the compounds of formula I or their (1-4C)alkoxycarbonyl derivatives defined above may exist in optically active or racemic forms by virtue of one or more substituents containing an asymmetric carbon atom, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intravascular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as gelatin or starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30μ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

The amount of active ingredient that is combined with one or more excipients to produce a single dosage form will necessarily vary depending upon the host treated and the particular route of administration. For example, a formulation intended for oral administration to humans will generally contain for example from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

The invention also includes a method of treating a disease or medical condition mediated alone or in part by one or more leukotrienes which comprises administering to a warm-blooded animal requiring such treatment an effective amount of an active ingredient as defined above (that is an indazolone of formula I or a pharmaceutically acceptable salt thereof; or a (1-4C)alkoxycarbonyl derivative thereof as defined above); or of an indazolone of formula I wherein Y is butyl or 4-methyl-, 4-ethoxy- or 4-methoxyphenyl, Ra is hydrogen, halogeno, methyl or ethyl and Rb is hydrogen; or wherein Y is a straight chain (2-5C)alkyl optionally bearing a terminally situated hydroxy substituent, or is unsubstituted phenyl or benzyl, or is benzyl bearing an acetyl substituent, and Ra and Rb are hydrogen; or a pharmaceutically acceptable salt thereof; or a (1-4C)alkoxycarbonyl derivative thereof. The invention also provides the use of such an active ingredient or indazolone of formula I as defined immediately above in the production of a new medicament for use in a leukotriene mediated disease or medical condition.

One particularly preferred known indazolone of formula I for use in such a method of treatment or manufacture of a novel medicament is, for example, 1,2-dihydro-2-benzyl-3H-indazol-3-one or a pharmaceutically acceptable salt thereof.

Particular values for the generic radicals referred to above are set out below.

A particular value for $A^1$ or $A^2$ when it is (1-6C)alkylene is, for example, methylene, ethylene, ethylidene, trimethylene, propylidene, tetramethylene or pentamethylene; when it is (3-6C)alkenylene is, for example, 1-propenylene, 2-propenylene, 1-butenylene, 2-butenylene or 3-butenylene; and when it is (3-6C)alkynylene is, for example, 2-propynylene, 2-butynylene or 3-butynylene.

A particular value for $A^1$ when it is cyclo(3-6C)alkylene is, for example, cyclopropylidene, 1,2-cyclopropylene, cyclopentylidene, 1,2-cyclopentylene, 1,3-cyclopentylene, cyclohexylidene or 1,4-cyclohexylene.

A particular value for a (1-4C)alkoxycarbonyl substituent which may be present on $A^1$ is, for example, methoxycarbonyl, ethoxycarbonyl or t-butoxycarbonyl.

Preferred values for $A^1$ include, for example, methylene and ethylidene.

A particular value for an optional substituent which may be present on $A^1$ when it is phenylene or on X when it is phenylene is for example, fluoro, chloro, bromo, trifluoromethyl, methyl, ethyl, propyl, methoxy, ethoxy, propoxy or isopropoxy.

A particular value for X when it is (1-6C)alkylimino is, for example, methylimino, ethylimino, propylimino or hexylimino, and when it is (1-6C)alkanoylimino is, for example, acetylimino, propionylimino or butyrylimino.

A particular value for Y when it is (2-10C)alkyl is, for example, ethyl, propyl, butyl, pentyl, neopentyl, hexyl or octyl, when it is (3-10C)alkenyl is, for example, allyl, allenyl, 2-methyl-2-propenyl or 3,5-hexadienyl and when it is (3-6C)alkynyl is, for example, 2-propynyl, 2-butynyl or 3-butynyl.

Particular values for the optional substituent which may be present when Y is (2-10C)alkyl, (3-10C)alkenyl or (3-6C)alkynyl include by way of example:

for (1-6C)alkoxy: methoxy, ethoxy, propoxy, isopropoxy, butoxy and hexyloxy;

for (1-6C)alkylthio: methylthio, ethylthio and propylthio;

for (1-6C)alkylsulphinyl: methylsulphinyl, ethylsulphinyl and propylsulphinyl;

for (1-6C)alkylsulphonyl: methylsulphonyl, ethylsulphonyl and propylsulphonyl;

for N-[(1-6C)alkyl]carbamoyl: N-methylcarbamoyl, N-ethylcarbamoyl and N-butylcarbamoyl;

for N,N-di[(1-4C)alkyl]carbamoyl: N,N-dimethylcarbamoyl and N,N-diethylcarbamoyl;

for (1-6C)alkylamino: methylamino, ethylamino and butylamino; and for di-[(1-4C)alkyl]amino: dimethylamino and diethylamino.

Particular values for Q when it is aryl or a hydrogenated derivative thereof, include, for example, phenyl, cyclohexyl, cyclohexenyl, naphthyl, tetrahydronaphthyl, indenyl and indanyl, which may be attached through any available position and which may bear one or two substituents.

Particular values for Q when it is heteroaryl or a hydrogenated derivative thereof, include, for example, furyl, benzofuranyl, tetrahydrofuryl, chromanyl, thienyl, pyridyl, quinolyl, isoquinolyl, pyrazinyl, pyrimidinyl, pyridazinyl, pyrrolyl, indolyl, imidazolyl, N-methylimidazolyl, benzimidazolyl, pyrazolyl, indazolyl, oxazolyl, isoxazolyl, thiazolyl, isothiazolyl, 1,2,3-triazolyl, 1,2,4-triazolyl, oxadiazolyl, furazanyl, and thiadiazolyl, which may be attached through any available position including through any available nitrogen atom and which may bear one or two substituents including a substituent on any available nitrogen atom.

Particular values for Ra or Rb and for optional substituents which may be present on a phenyl, phenoxy or thiophenoxy substituent as defined above include the following, by way of example:

| | |
|---|---|
| for halogeno: | fluoro, chloro, bromo and iodo; |
| for (1-6C)alkyl: | methyl, ethyl, propyl, isopropyl and butyl; |
| for (1-6C)alkoxy: | methoxy, ethoxy, propoxy, isopropoxy and butoxy; |
| for fluoro-(1-4C)alkyl: | trifluoromethyl, 2,2,2-trifluoroethyl and pentafluoroethyl; |
| for (2-6C)alkanoyl: | acetyl, propionyl, butyryl and hexanoyl; |
| for (1-6C)alkylamino: | methylamino, ethylamino, propylamino, butylamino, pentylamino and hexylamino; |
| for di-[(1-4C)alkyl]amino: | dimethylamino, diethylamino and dipropylamino; |
| for (1-6C)alkylcarbamoyl: | N-methylcarbamoyl, N-ethylcarbamoyl and N-propylcarbamoyl; |

| -continued | |
|---|---|
| for di-[(1-4C)alkyl]-carbamoyl: | N,N-dimethylcarbamoyl and N,N-diethylcarbamoyl; |
| for (2-6C)alkanoylamino: | acetamido, propionamido, butyramido and hexanamido; |
| for hydroxy-(1-6C)alkyl: | hydroxymethyl, 2-hydroxyethyl, 1-hydroxyethyl and 3-hydroxypropyl; |
| for (2-6C)alkanoyloxy: | acetoxy, propionyloxy and butyryloxy. |

Particular values for optional substituents which may be present when Q is aryl or heteroaryl, or a hydrogenated derivative thereof, include by way of example:

| for (1-10C)alkyl: | methyl, ethyl, propyl, butyl, hexyl, and octyl; |
|---|---|
| for (1-10C)alkoxy: | methoxy, ethoxy, propoxy, isopropoxy, butoxy, 1-methylhexyloxy and nonyloxy; |
| for halogeno: | fluoro, chloro and bromo; |
| for fluoro-(1-4C)alkyl: | trifluoromethyl and pentafluoroethyl; |
| for phenyl (1-4C)alkyl: | benzyl, phenethyl, phenylpropyl and phenylbutyl; |
| for (2-6C)alkanoyl: | acetyl, propionyl, butyryl and hexanoyl; |
| for (1-6C)alkythio: | methylthio, ethylthio and butylthio; |
| for (1-6C)alkylsulphinyl: | methylsulphinyl, ethylsulphinyl and butylsulphinyl; |
| for (1-6C)alkylsulphonyl: | methylsulphonyl, ethylsulphonyl and butylsulphonyl; |
| for (1-6C)alkylamino: | methylamino, ethylamino propylamino, butylamino, pentylamino and hexylamino; |
| for di-[(1-4C)alkyl]amino: | dimethylamino, diethylamino and dipropylamino; |
| for (2-6C)alkanoylamino: | acetamido, propionamido and butyramido; |
| for di-[(2-6C)alkanoyl]-amino: | diacetylamino and dipropionylamino; |
| for hydroxy-(1-6C)alkyl: | hydroxymethyl, 1-hydroxyethyl, 2-hydroxyethyl, 1-hydroxypropyl, 1-hydroxypentyl and 1-hydroxyhexyl; |
| for (1-4C)alkylenedioxy: | methylenedioxy and ethylenedioxy; |
| for (2-10C)alkenyl: | vinyl, 1-propenyl, allyl, 2-methyl-2-propenyl and 3,5 hexadienyl; |
| for (1-6C)alkylcarbamoyl: | N-methylcarbamoyl, N-ethylcarbamoyl and N-propyl carbamoyl; |
| for di-[(1-4C)-alkyl]carbamoyl: | N,N-dimethylcarbamoyl and N,N-diethylcarbamoyl; |
| for (1-4C)alkoxycarbonyl: | methoxycarbonyl, ethoxycarbonyl and t-butoxycarbonyl. |

A particular value for a (1-4C)alkoxycarbonyl derivative of an indazolone of formula I is, for example, a methoxycarbonyl, ethoxycarbonyl or t-butoxycarbonyl derivative in which the alkoxycarbonyl group is located on N1 of the indazole ring.

Suitable pharmaceutically acceptable salts include, for example, alkali metal (such as potassium or sodium), alkaline earth metal (such as calcium or magnesium), ammonium and aluminium salts, and salts with organic bases affording physiologically acceptable cations, such as salts with methylamine, dimethylamine, trimethylamine, piperidine and morpholine. In addition, for those active ingredients which are sufficiently basic (for example those which contain an alkylamino or dialkylamino group), suitable pharmaceutically acceptable salts include physiologically acceptable acid-addition salts such as salts with hydrogen halides, sulphuric acid, phosphoric acid, citric acid and maleic acid.

Certain of the active ingredients of formula I are known, for example those compounds of formula I wherein Ra is hydrogen, 5-methyl or 5-chloro, Rb=H and Y is 4-methyl- or 4-methoxy-phenyl, and wherein Ra is hydrogen, Rb=H and Y is 4-ethoxyphenyl are described in Japanese patent publication No. 72.29900 (*Chemical Abstracts, Vol* 77, 140065 q) and in *J. Heterocyclic Chemistry* 1970, 7, 815–820 as chemical intermediates and possible anti-inflammatory agents. Similarly, those compounds of formula I wherein Ra and Rb are hydrogen and Y is ethyl, propyl, butyl, pentyl, 2-hydroxyethyl, 3-hydroxypropyl, phenyl, benzyl, or 2-, 3- or 4-acetylbenzyl, are described in *J. Medicinal Chemistry* 1984, 27, 768–772 as potential anti-hypertensive agents. However, hitherto it has not been known that the compounds of formula I possess the property of inhibiting the enzyme 5-LO and are of value as therapeutic agents in the prevention or treatment of those diseases in which such inhibition of 5-LO is desirable.

A specific known indazolone of formula I which is of particular interest as an inhibitor of 5-LO is, for example, 1,2-dihydro-2-benzylindazol-3-one. Although this compound is said to have weak anti-inflammatory properties in carrageenin induced oedema in rat paws (*J. Heterocyclic Chemistry*, 1970, 7, 815–820), we have been unable to detect any significant effects for the compound dosed orally at 100 mg/kg in this test system.

The majority of the compounds of formula I are novel. The invention further provides a novel group of indazolones of the formula I wherein Ra, Rb and Y have the meanings defined above, provided that, in addition to the previous disclaimer, when Y is phenyl, Ra is other than nitro, chloro, dimethylamino, methyl or methoxy; when Y is tolyl, Ra is other than hydrogen, methyl, chloro or nitro; when Y is chlorophenyl, Ra is other than hydrogen or chloro; when Y is 4-chlorobenzyl, 4-methoxybenzyl or 2-hydroxyphenyl Ra is other than hydrogen; when Y is 2-hydroxy-5-t-butylphenyl, Ra is other than hydrogen or methyl; and when Y is 2-pyridyl or 2-carboxyphenyl, Ra is other than hydrogen or chloro; together with the pharmaceutically acceptable salts thereof; and the (1-4C)alkoxycarbonyl derivatives thereof.

Particular values for the generic radicals Y, Ra and Rb are, for example, those defined hereinabove subject to the above mentioned exclusions.

Particular groups of novel compounds of the invention include those compounds of formula I wherein:
(i) Ra has any of the meanings defined hereinbefore except hydrogen, and Rb and Y have any of the meanings defined hereinbefore;
(ii) the carbon atom in Y at the point of attachment to the indazolone nitrogen atom bears one or no hydrogen substituent, and Ra and Rb have any of the meanings defined above;
(iii) Y is a group of the formula —A$^1$—X—A$^2$—Q wherein A$^1$, X and A$^2$ have any of the meanings defined hereinbefore, but the linking group —A$^1$—X—A$^2$— contains at least one linking atom and the linking group is other than methylene when Q is phenyl, acetylphenyl, 4-methoxyphenyl or 4-chlorophenyl, and Ra and Rb have any of the meanings defined hereinbefore;
(iv) Y is benzyl bearing two substituents as defined hereinbefore for Q, and Ra and Rb have any of the meanings defined hereinbefore;

(v) Y is benzyl optionally bearing one or two substituents as defined hereinbefore for Q and Ra and Rb have any of the meanings defined hereinbefore, but Y is not acetylbenzyl, 4-methoxybenzyl, 4-chlorobenzyl or benzyl when Ra and Rb are both hydrogen;

(vi) Y is a group of the formula $-A^1-X-A^2-Q$ wherein $A^1$, X and $A^2$ have any of the meanings defined hereinbefore, Q is a 6-membered heteroaryl containing one or two nitrogen atoms which may optionally bear one or two substituents as defined hereinbefore for Q and Ra and Rb have any of the meanings defined hereinbefore, but when Y is 2-pyridyl, Ra is other than hydrogen or chloro;

(vii) Y is a group of the formula $-A^1-X-A^2-Q$ wherein $A^1$, X and $A^2$ have any of the meanings defined hereinbefore, Q is quinolyl or isoquinolyl which may optionally bear one or two substituents as defined hereinbefore for Q and Ra and Rb have any of the meanings defined hereinbefore; or (viii) Y is a group of the formula $-A^1-X-A^2-Q$ wherein $A^1$, X and $A^2$ have any of the meanings defined hereinbefore, Q is a 5-membered heteroaryl containing one or more (especially one or two) nitrogen atoms optionally together with a sulphur or oxygen atom or a benz fused derivative thereof and which heteroaryl or benz fused derivative thereof may optionally bear one or two substituents as defined hereinbefore for Q and Ra and Rb have any of the meanings defined hereinbefore; together in each group with the pharmaceutically acceptable salts thereof; and the (1-4C)alkoxycarbonyl derivatives thereof.

Particular values for the generic radical Q when it is a 6-membered heteroaryl containing one or two nitrogen atoms include, for example, pyridyl, pyrazinyl, pyrimidinyl and pyridazinyl.

Particular values for the generic radical Q when it is a 5-membered heteroaryl containing one or more (especially one or two) nitrogen atoms optionally together with a sulphur or oxygen atom or a benz fused derivative thereof include, for example, pyrrolyl, imidazolyl, N-methylimidazolyl, pyrazolyl, oxazolyl, isoxazolyl, thiazolyl, isothiazolyl, 1,2,3-triazolyl, 1,2,4-triazolyl, oxadiazolyl, furazanyl, thiadiazolyl, indolyl, benzimidazolyl and indazolyl.

A preferred group of novel compounds of the invention includes those compounds of formula I wherein Ra is hydrogen, halogeno or (1-6C)alkyl (especially hydrogen, fluoro, chloro or methyl); Rb is hydrogen; and Y is a group of the formula $-A^1-X-A^2-Q$ in which $A^1$ is methylene or ethylidene, X is a direct link to $A^2$, $A^2$ is a direct link to Q or the group $-A^1-X-A^2-$ is a direct link to Q; and Q is phenyl, thienyl, pyridyl, thiazolyl or benzimidazolyl, which may optionally bear a substituent selected from (1-4C)alkyl, (1-4C)alkoxy, halogeno, hydroxy, di-[(1-4C)alkyl]amino, cyano and hydroxy-(1-6C)alkyl (especially methyl, methoxy, fluoro, chloro, bromo, hydroxy, dimethylamino, cyano and 1-hydroxypropyl); provided that this group of novel compounds is subject to the above mentioned disclaimers; together with the pharmaceutically acceptable salts thereof.

A particularly preferred group of novel compounds of the invention includes those compounds of formula I wherein Ra and Rb are both hydrogen; and Y is a group of the formula $-A^1-X-A^2-Q$ in which $A^1$ is methylene or ethylidene; X is a direct link to $A^2$, $A^2$ is a direct link to Q; and Q is 3-pyridyl or 4-pyridyl; together with the pharmaceutically acceptable salts thereof.

Specific novel compounds of formula I are illustrated in the accompanying Examples. However, of these Examples, three compounds of particular interest are those described in Examples 24, 58 and 60 which are provided together with their pharmaceutically acceptable salts as a further feature of the invention.

A further preferred group of novel compounds of the invention includes those compounds of formula I wherein Ra is hydrogen, halogeno, (1-6C)alkyl or (1-6C)alkoxy (especially hydrogen, fluoro, chloro, methyl, methoxy or butoxy); Rb is hydrogen; and Y is a group of the formula $-A^1-X-A^2-Q$ in which $A^1$ is (1-6C)alkylene, (3-6C)alkenylene or cyclo(3-6C)alkylene (especially methylene, ethylene, trimethylene, ethylidene, propylidene, 2-propenylene, 1,2-cyclopropylene or cyclopropylidene), X is oxy, imino or a direct link to $A^2$, $A^2$ is methylene or a direct link to Q or the group $-A^1-X-A^2-$ is a direct link to Q, and Q is a 6-membered heteroaryl containing one or two nitrogen atoms (especially pyridyl or pyrazinyl) which may optionally bear one or two substituents selected from (1-10C)alkyl, (1-10C)alkoxy, halogeno and cyano (especially methyl, ethyl, methoxy, bromo, chloro and cyano), provided that when Y is 2-pyridyl, Ra is other than hydrogen or chloro, or Q is a 5-membered heteroaryl containing one or more (especially one or two) nitrogen atoms optionally together with a sulphur or oxygen atom or a benz fused derivative thereof (especially furyl, thienyl, imidazolyl, pyrazolyl, isoxazolyl, thiazolyl, thiadiazolyl or benzimidazolyl) and which heteroaryl may optionally bear one or two substituents selected from (1-10C)alkyl, amino, phenyl-(1-4C)alkyl and (2-6C)alkanoylamino (especially methyl, amino, benzyl and acetamido); or Y is naphthylmethyl; or Y is benzyl optionally bearing one or two substituents selected from (1-10C)alkyl, (1-10C)alkoxy, halogeno, nitro, hydroxy, amino, di-[(1-4C)alkyl]amino, cyano, phenyl, fluoro-(1-4C)alkyl, (2-6C)alkanoylamino, di-[(2-6C)alkanoyl]amino and hydroxy-(1-6C)alkyl (especially methyl, methoxy, bromo, chloro, nitro, hydroxy, amino, dimethylamino, cyano, phenyl, trifluoromethyl, acetamido, diacetylamino and 1-hydroxypropyl) or Y is benzyl optionally bearing a (1-4C)alkylenedioxy substituent (especially methylenedioxy), provided that Y is not acetylbenzyl, 4-methoxybenzyl, 4-chlorobenzyl or benzyl when Ra and Rb are both hydrogen; or Y is (3-10C)alkenyl or (3-6C)alkynyl (especially allenyl or 2-propynyl); together with the pharmaceutically acceptable salts thereof.

A further particularly preferred group of novel compounds of the invention includes those compounds of formula I wherein Ra is hydrogen or methyl; Rb is hydrogen; and Y is a group of the formula $-A^1-X-A^2-Q$ in which $A^1$ is methylene or ethylene, X is a direct link to $A^2$, $A^2$ is a direct link to Q and Q is 3-pyridyl or 4-pyridyl which may optionally bear a substituent selected from methyl, ethyl, methoxy, bromo and chloro, or Q is 2-thienyl, 3,5-dimethylisoxazol-4-yl, 5-thiazolyl, 1,2,5-thiadiazol-3-yl or 1,2,3-thiadiazol-4-yl; together with the pharmaceutically acceptable salts thereof.

A further particularly preferred group of novel compounds of the invention includes those compounds of formula I wherein Ra is hydrogen, methyl or fluoro; Rb is hydrogen; and Y is benzyl optionally bearing one or two substituents selected from methyl, methoxy, nitro and amino or one methylenedioxy substituent, provided that Y is not acetylbenzyl, 4-methoxybenzyl, 4-chlorobenzyl or benzyl when Ra and Rb are both hydrogen; together with the pharmaceutically acceptable salts thereof.

Specific novel compounds of formula I are illustrated in the accompanying Examples. However, of these Examples, seven further compounds of particular interest are those described in Examples 117, 123, 151, 239, 246, 247 and 248 which are provided together with their pharmaceutically acceptable salts as a further feature of the invention.

The compounds of formula I may be obtained by conventional procedures of organic chemistry well known in the art for the manufacture of structurally analogous indazolones. Thus, for example, they may be obtained by the procedures analogous to those disclosed in "The Chemistry of Heterocyclic Compounds", (ed. R. H. Wiley, published by Interscience 1967), Vol. 22, Chapter 10, at pages 356–361, in "The Heterocyclic Compounds". (ed. R. C. Elderfield, published by Wiley 1957), Vol. 5, at pages 166–182, and in the article by L. Baiocchi and G. Palazzo (Synthesis, 1978, 633–648), the contents of which publications are incorporated herein by way of reference. The invention further includes the manufacture of a novel compound of formula I, or of a (1-4C)alkoxycarbonyl derivative thereof, or of a pharmaceutically acceptable salt thereof, by any one of such analogous procedures.

In particular, the invention includes the manufacture of novel compounds of formula I defined above by a process (a) which comprises deprotecting a protected indazolone derivative of the formula II wherein Ra and Rb have the meanings defined hereinbefore and Rd is a protecting group.

Suitable examples of protecting groups Rd include, for example, acyl groups such as (1-4C)alkanoyl (especially acetyl), (1-4C)alkoxycarbonyl (especially methoxcarbonyl, ethoxycarbonyl and t-butoxycarbonyl) and aroyl (especially benzoyl). The deprotection conditions used for the above process necessarily vary with the nature of Rd. Thus, for example, acyl groups such as alkanoyl, alkoxycarbonyl and aroyl may be removed, for example by hydrolysis with base such as an alkali metal hydroxide (for example lithium or sodium hydroxide) or acid such as hydrochloric, sulphuric or phosphoric acid, generally in the presence of an aqueous solvent or diluent such as a (1-4C)alkanol and at a temperature in the range, for example, 0° to 60° C. (conveniently at or about room temperature). It will be appreciated that, when a base is used for the deprotection, the indazolone is initially formed as the corresponding salt from which the free indazolone may be liberated by a conventional acidification process, for example by treatment with a mineral acid such as hydrochloric acid. The process is particularly adapted to the production of those compounds of formula I wherein Y is alkyl, alkenyl or a group —$A^1.X.A^2$—Q as previously defined but wherein —$A^1.X.A^2$— is other than a direct link to Q.

The starting materials of formula II may be conveniently obtained, for example, by protecting the dihydropyrazolone moiety of an indazolone derivative of the formula III, for example by reacting it with a suitable acyl halide, or anhydride, such as a (1-4C)alkanoyl chloride or bromide, a (1-4C)alkanoic acid anhydride, benzoyl chloride, benzoic acid anhydride, or a (1-4C)alkoxycarbonyl chloride (which is preferred) under conventional acylation conditions, for example in the presence of a suitable base such as pyridine, 4-dimethylaminopyridine, triethylamine, morpholine or N-methylmorpholine, to give a protected derivative of formula IV wherein Rd has the meanings defined above. The latter derivative may then be reacted with an alkylating agent of the formula L-Y wherein L is a leaving group and Y has the meaning defined hereinabove. Suitable leaving groups, when Y is alkyl or alkenyl, or is a group of the formula —$A^1.X.A^2$.Q in which —$A^1.X.A^2$— is other than a direct link to Q, include, for example halogeno (especially chloro, bromo or iodo) and alkane- or arene-sulphonyloxy (especially methansulphonyloxy or p-toluenesulphonyloxy). The alkylation reaction is preferably performed in the presence of a suitable base, for example an alkali metal hydroxide in a suitable inert solvent or diluent, for example, t-butyl methyl ether, tetrahydrofuran, 1,2-dimethoxyethane, N-methylpyrrolidone, or N,N-dimethylformamide. Alternatively, the protected indazole derivative of formula IV may be used in the form of its preformed anhydrous alkali metal salt, for example by prior reaction with a molecular equivalent of a suitable base such as sodium or potassium methoxide, ethoxide or hydride or butyl-lithium; in which case a wider range of conventional solvents such as (1-4C)alkanol diluents may be employed for the reaction with the alkylating agent of formula L-Y. This procedure is particularly useful when Rd is a (1-4C)alkoxycarbonyl group. In either case, the alkylation is generally preformed at a temperature in the range, for example, 10° to 100° C. and, conveniently, at or near ambient temperature.

It is to be understood that the reaction of protected derivatives of formula IV with an alkylating agent of the formula L-Y may, in addition, give rise to a compound isomeric with that of formula II i.e. in which Y is attached to the oxygen atom of the amide group. Such isomeric compounds may be separated by procedures well known to those skilled in the art, for example by column chromatography or by crystallisation.

The starting indazole derivatives of formula III may be made by analogy with known synthetic procedures.

A further process (b) according to the invention for the manufacture of a novel compound of formula I as defined hereinbefore comprises cyclising a 2-hydrazinobenzoic acid of the formula V, or a reactive derivative thereof, wherein Ra and Rb have the meanings defined above.

The cyclisation may be carried out using a variety of conditions. For example, it may be carried out thermally by heating the free carboxylic acid at a temperature in the range, for example, 40–120° C., under the influence of an acid catalyst such as acetic acid, propionic acid or a mineral acid (for example hydrochloric, sulphuric or phosphoric acid). Alternatively, the free carboxylic acid may be converted to a reactive derivative such as an acid halide, for example using phosphoryl chloride, oxalyl chloride or thionyl chloride at a temperature in the range, for example, 10° to 60° C., which halide may in certain cases spontaneously cyclise to the required indazolone of formula I. An alternative reactive derivative of the carboxylic acid of formula V is, for example, a (1-4C)alkyl, phenyl or benzyl ester of said acid, which derivatives may be cyclised, for example, by the influence of heat, optionally in the presence of an acid or basic catalyst.

The starting 2-hydrazinobenzoic acids of formula V may be obtained, by standard procedures of organic chemistry. Thus, for example, those compounds of formula V wherein Y is a group of the formula —CH$_2$—A$^3$—X—A$^2$—Q in which A$^3$ is (1-5C)alklene, (3-5C)alkenylene or (3-5C)alkynylene optionally bearing a substituent as defined hereinbefore for A$^1$ and Q, X and A$^2$ have the meanings defined hereinbefore, or the group —A$^3$—X—A$^2$— is a direct link to Q, or Y is a group of the formula —CH$_2$.Y$^1$ in which Y$^1$ is (2-9C)alkyl or (3-9C)alkenyl optionally substituted as defined hereinbefore for Y when it is alkyl or alkenyl; may be obtained by reduction of a hydrazone of the formula VIa or VIb, for example using an alkali metal amalgam, borohydride or cyanoborohydride (especially sodium cyanoborohydride) in a suitable solvent or diluent such as a (1-4C)alkanol (for example ethanol or methanol) or an ether (for example tetrahydrofuran or t-butyl methyl ether) at a temperature in the range, for example, 10° to 50° C. The hydrazones of formula VIa or VIb may themselves be obtained by a conventional procedure involving reaction of an aldehyde of the formula H.CO.A$^3$.X.A$^2$.Q or H.CO.Y$^1$ with a hydrazine of the formula VII. The hydrazines of formula VII may themselves be obtained, for example, by a conventional reduction of a diazonium salt derived from the corresponding 2-aminobenzoic acid, for example using sodium sulphite, sulphur dioxide or stannous chloride as a reducing agent. The necessary 2-aminobenzoic acids and the aldehydes of the formula H.CO.A$^3$.X.A$^2$.Q or H.CO.Y$^1$ are in general known or may be obtained by standard procedures of organic chemistry.

As will readily be appreciated process (b) is particularly suitable for the production of those compounds of formula I wherein Y is a group of the formula —CH$_2$Q or —CH$_2$Y$^1$ as defined above.

A further process (c) according to the invention for the manufacture of a novel compound of formula I comprises cyclising a 2-aminobenzamide derivative of the formula VIII wherein Z is a suitable leaving group, for example hydroxy, acetoxy, methoxy or p-toluenesulphonyloxy.

The cyclisation may be carried out using a variety of conditions. For example, it may be carried out under conventional acid or base catalysis (which latter is generally preferred) at a temperature in the range, for example 40° to 120° C., in a suitable solvent or diluent for example a (1-4C)alkanol (such as methanol or ethanol). A suitable base is, for example, an alkali metal hydroxide or (1-4C)alkoxide, such as sodium hydroxide, potassium hydroxide, sodium methoxide or potassium ethoxide.

The starting materials of formula VIII can be made by standard techniques of organic chemistry. Thus, for example, those compounds of formula VIII wherein Z is hydroxy may be obtained by reduction of the corresponding nitro compound of formula IX using conditions known to produce the required hydroxylamine, for example using zinc or iron dust in the presence of a base such as an alkali metal hydroxide or ammonium acetate, at a temperature in the range, for example, 10° to 50° C. and in a suitable aqueous solvent of diluent such as methanol or ethanol.

The production of a novel compound of formula I may therefore also be carried out by the preferred procedure of reacting a nitro compound of formula IX with a suitable reducing metal, such as zinc or iron dust, in the presence of a strong base, such as an alkali metal hydroxide, in a suitable solvent or diluent such as a (1-4C)alkanol (e.g. methanol or ethanol, of which the latter is preferred), and at a temperature in the range, for example, 40° to 120° C.

The starting materials of formula IX may be obtained from the corresponding carboxylic acids of formula X and the amines of formula H$_2$N.Y using conventional amidification procedures such as those illustrated in the accompanying Examples.

A further process (d) according to the invention for the production of a novel compound of formula I wherein Y is the group Q comprises isomerising a 2-hydroxy-3-substituted -2H-indazole derivative of the formula XI or an alkali metal salt thereof or alkali metal sulphite complex therewith.

The isomerisation is generally performed by heating a compound of formula XI in the presence of a suitable base such as an alkali metal hydroxide (e.g. sodium hydroxide) in a suitable aqueous solvent or diluent, such as water or a (1-4C)alkanol, at a temperature in the range, for example, 60° to 120° C.

The starting materials of formula XI may be obtained, for example, by reduction of a diazonium salt obtained from an aniline derivative of the formula XII with sodium sulphite, in which case a sulphite complex of the compound of formula XI is generally obtained. A convenient variation of the process (d) thus comprises reducing a diazonium salt (for example a diazonium chloride or bromide) derived from an aniline of formula XII with a suitable reducing agent known to convert the diazonium linkage to a hydrazino group, for example sodium sulphite, and then heating the intermediate product with an alkali metal hydroxide such as sodium or potassium hydroxide at a temperature in the range, for example, 60° to 120° C.

A further process (e) according to the invention for the production of those novel compounds of formula I wherein Y is a group of the formula —A$^1$—X—A$^2$—Q and wherein X is sulphinyl or sulphonyl, or wherein one or more of the other substituents is alkylsulphinyl or alkylsulphonyl, comprises oxidising a compound of formula I wherein Y is a group of the formula —A$^1$—X—A$^2$—Q and wherein X is thio, and/or wherein one or more of the other substituents is alkylthio.

A particular suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, acetone, tetrahydrofuran or t-butyl methyl ether and at a temperature, for example, at or near ambient temperature, that is in the range 15° to 35° C. When a compound wherein X is sulphinyl and/or one of the other substituents is alkylsulphinyl is required, a milder oxidising agent may also be used, for example sodium or potassium metaperiodate, conveniently in a polar solvent such as acetic acid. It will be appreciated that when a compound of formula I containing a sulphonyl group is required, it may be obtained by oxidation of the corresponding sulphinyl compound as well as of the corresponding thio compound.

A further process (f) according to the invention for the manufacture of those novel compounds of formula I which contain one or more phenolic hydroxy groups comprises deprotecting a protected version of such a compound of formula I.

Suitable phenolic hydroxy protecting groups include, for example, (1-6C)alkyl, (3-6C)alk-2-enyl, tri(1-4C)alkylsilyl tetrahydropyran-2-yl, 1-aryl-(1-4C)alkyl, (1-6C)alkanoyl and aroyl (such as methyl, ethyl, t-butyl, allyl, trimethylsilyl, tetrahydropyran-2-yl, benzyl, 1-phenylethyl, formyl, acetyl and benzoyl).

The deprotection reaction conditions necessarily depend on the protecting group used. However, in general, conditions which are standard in the art for the removal of the same protecting group in chemically analogous compounds are used. Thus, for example, when the protecting group is (1-6C)alkyl (and especially methyl) the deprotection may be carried out, for example, by use of boron tribromide at $-80°$ to $20°$ C., optionally in a suitable solvent such as methylene chloride, or by heating with sodium thioethoxide in a suitable solvent, such as N,N-dimethylformamide or 1,3-dimethyl-3,4,5,6-tetrahydro-2(1H)-pyrimidinone, at a temperature of, for example, $50°$ to $160°$ C. Alternatively, an ethyl or methyl protecting group may be removed, for example, by reaction with lithium diphenylphosphide in a suitable solvent or diluent, such as tetrahydrofuran or t-butyl methyl ether, at a temperature in the range, for example, $0°$ to $60°$ C. Similarly, an alkanoyl or benzoyl protecting group may be removed, for example, by base catalysed hydrolysis (such as sodium or potassium hydroxide in an aqueous (1-4C)alkanol or glycol) at a temperature, for example, in the range $10°$ to $60°$ C. Similarly, an allyl or tetrahydropyran-2-yl protecting group may be removed, for example, by a conventional treatment with a strong acid such as trifluoroacetic acid. Similarly, a trimethylsilyl protecting group may be removed, for example, by conventional treatment with aqueous tetrabutylammonium fluoride or sodium fluoride, and a benzyl or 1-phenylethyl protecting group, for example, by treatment with sodium in liquid ammonia.

The necessary protected derivatives are obtainable by analogous procedures to those described hereinbefore or by modifications thereto within the ordinary skill of an organic chemist.

A further process (g) according to the invention for the production of those novel compounds of formulae I or II which contain one or more alkanoylamino or dialkanoylamino groups comprises acylating a compound of formula I or a compound of formula II which contains one or more amino groups.

A particular suitable acylating agent is, for example, any agent known in the art for the acylation of amino to acylamino and/or diacylamino, for example an acyl halide, for example a (2-6C)alkanoyl chloride or bromide, in the presence of a suitable base, an alkanoic acid anhydride, for example a (2-6C)alkanoic acid anhydride, or an alkanoic acid mixed anhydride, for example the mixed anhydride formed by the reaction of an alkanoic acid and a (1-4C)alkoxycarbonyl halide, for example a (1-4C)alkoxycarbonyl chloride, in the presence of a suitable base. In general the reaction is carried out in a suitable solvent or diluent such as methylene chloride, acetone, tetrahydrofuran or t-butyl methyl ether and at a temperature, for example, at or near ambient temperature, that is in the range $15°$ to $35°$ C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate. It will be appreciated that when a compound of formula I or a compound of formula II containing a diacylamino group is required, it may be obtained by acylation of the corresponding acylamino compound as well as the corresponding amino compound. It will also be appreciated that when a compound of formula I which contains one or more amino groups is subjected to reaction with an acylating agent there may be, in addition to acylation of the amino group, acylation of the unprotected nitrogen atom in the indazolone ring. It is well known to one skilled in the art how to separate such mixtures of compounds, for example by column chromatography or by crystallisation. It will also be appreciated that when a compound of formula II is acylated a novel compound of formula I can be produced by deprotecting the protected indazolone using conditions described under process (a) above.

A further process (h) according to the invention for the production of those novel compounds of formula I wherein Ra is amino, or Y is a group of the formula $-A^1-X-A^2-Q$ or the group $-A^1-X-A^2-Q$ is a direct link to Q and there are one or more amino substituents in Q, comprises the reduction of the corresponding compound wherein Ra is nitro or there are one or more nitro substituents in Q. In general conditions which are standard in the art for the reduction of a nitro group are used. Thus, for example, the reduction may be carried out by the hydrogenation of a solution of the nitro compound in an inert solvent or diluent in the presence of a suitable metal catalyst, for example finely divided platinum metal (obtained by the reduction of platinum oxide in situ). A suitable inert solvent or diluent is, for example, an alcohol, for example methanol, ethanol or isopropanol, or an ether, for example tetrahydrofuran or t-butyl methyl ether. The reaction is generally carried out at a temperature at or near ambient temperature, that is in the range $15°$ to $35°$ C.

A further process (i) according to the invention for the production of those novel compounds of formula I wherein Y is a group of the formula $-A^1-X-A^2-Q$ and wherein $A^1$ or $A^2$ is alkynylene comprises the reduction of the corresponding compound wherein $A^1$ or $A^2$ is alkynylene. In general conditions which are standard in the art for the reduction of an alkynylene group are used. Thus, for example, the reduction may be carried out by the hydrogenation of a solution of the alkynylene compound in an inert solvent or diluent in the presence of a suitable metal catalyst. A suitable inert solvent is, for example, an alcohol, for example methanol or ethanol, or an ether, for example tetrahydrofuran or t-butyl methyl ether. A suitable metal catalyst is, for example, palladium or platinum on an inert support, for example charcoal or barium sulphate.

Preferably a palladium-on-barium sulphate catalyst is used to substantially prevent over-reduction of the alkynylene group to an alkylene group. The reaction is generally carried out at a temperature at or near ambient temperature, that is in the range $15°$ to $35°$ C.

When a pharmaceutically acceptable salt of a novel compound of formula I is required, it may be obtained, for example, by reaction of said compound with a suitable acid or base using a conventional procedure. When an optically active form of a compound of formula I is required, it may be obtained by carrying out one of the aforesaid procedures using an optically active starting material, or by resolution of a racemic form of said compound using a conventional procedure.

Certain of the intermediates described herein are novel, for example the hydroxylamines of formula VIII (Z=hydroxy) and the corresponding nitro precursors of formula IX. These novel intermediates are provided as a separate feature of the invention.

As stated previously, the indazolones of formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512-11519). This test provides a measure of the intrinsic inhibitory properties against soluble 5-LO in an extracellular environment.

b) An in vitro assay system involving incubating a test compound with heparinised rat blood, prior to challenge with the calcium ionophore A23187 and then indirectly measuring the inhibitory effects on 5-LO by assaying the amount of $LTB_4$ using the specific radioimmunoassay described by Carey and Forder (F. Carey and R. A. Forder, *Brit. J. Pharmacol.* 1985, 84, 34P) which involves the use of a protein-$LTB_4$ conjugate produced using the procedure of Young et alia (*Prostaglandins*, 1983, 26(4), 605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for prostaglandin $E_2(PGE_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test (b) above, involving administration of a test compound (usually orally as a suspension in carboxymethylcellulose)blood collection, heparinisation, challenge with A23187 and radioimmunoassay of $LTB_4$ and $PGE_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol.*, 1983, 32, 2319-2322) and conventional radioimmunoassay systems to measure $LTC_4$ and $PGE_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the mouse ear model developed by J. M. Young et alia (*J. Investigative Dermatology*, 1984, 582(4), 367-371. This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a $\beta$-adrenergic blocking agent (propranolol) and a cyclooxygenase inhibitor (indomethacin), using the procedure of W. H. Anderson et alia (*British J Pharmacology*, 1983, 78(1), 67-574).

This test provides a further in vivo test for detecting 5-LO inhibitors.

Although the pharmacological properties of the compounds of formula I vary with structural changes as expected, in general compounds of formula I possess 5-LO inhibitory effects at the following concentrations or doses in one or more of the above tests (a)-(f):

Test (a): $IC_{50}$ in the range, for example, 0.1-30 $\mu$M;

Test (b): $IC_{50}$ ($LTB_4$) in the range, for example, 0.2-5 $\mu$M $IC_{50}$ ($PGE_2$) in the range, for example, 15-200 $\mu$M;

Test (c): oral $ED_{50}$ ($LTB_4$) in the range, for example, 1-100 mg/kg; oral $ED_{50}$ ($PGE_2$) in the range, for example 30-200 mg/kg.

Test (d): $IC_{50}$ ($LTC_4$) in the range, for example, 0.1-10 $\mu$M $IC_{50}$ ($PGE_2$) in the range, for example, 20-1000 $\mu$M;

Test (e): topical $IC_{50}$ in the range, for example, 0.3-100 $\mu$g/ear;

Test (f): $ED_{50}$ in the range, for example, 0.5-10 mg/kg i.v.

No overt toxicity or other untoward effects are present in tests (c), (e) and/or (f) when compounds of formula I are administered at several multiples of their minimum inhibitory dose or concentration.

Thus, by way of example, the novel compound 1,2-dihydro-2-(1-naphthylmethyl)-3H-indazol-3-one has an $IC_{50}$ of 1.7 $\mu$M in test (a), an $IC_{50}$ of 0.8 $\mu$M against $LTB_4$ and of 100 $\mu$M against $PGE_2$ in test (b), and an oral $ED_{50}$ of 30 mg/kg versus $LTB_4$ in the test (c). In general those compounds of formula I which are particularly preferred, for example the compound of Example 24, have an $IC_{50}$ of $<5$ $\mu$M against $LTB_4$ and of $>100$ $\mu$M against $PGE_2$ in test (b), and an oral $ED_{50}$ of $<10$ mg/kg against $LTB_4$ and of $>100$ mg/kg against $PGE_2$ in test (c).

These compounds are examples of indazolones of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

The size of the dose for therapeutic or prophylactic purposes of an indazolone of formula I will naturally vary according to the nature and severity of the conditions, the age and sex of the animal or patient and the route of administration, according to well known principles of medicine. As mentioned above, the indazolones of formula I are useful in treating those allergic and inflammatory conditions which are due alone or in part to the effects of the metabolites of arachidonic acid arising by the linear (5-LO catalysed) pathway and in particular the leukotrienes, the production of which is set in train by 5-LO. As previously mentioned, such conditions include, for example, asthmatic conditions, allergic reactions, allergic rhinitis, allergic shock, psoriasis, atopic dermatitis, cardiovascular and cerebrovascular disorders or an inflammatory nature, arthritic and inflammatory joint disease, and inflammatory bowel disease.

In using a compound of formula I for therapeutic or prophylactic purposes it will generally be administered so that a daily dose in the range, for example, 0.1 mg to 75 mg per kg body weight is received, given if required in divided doses. In general lower doses will be administered when a parenteral route is employed. Thus, for example, for intravenous administration, a dose in the range, for example, 0.1 mg to 30 mg per kg body weight will generally be used. Similarly, for administration by inhalation, a dose in the range, for example, 0.1 mg to 25 mg per kg body weight will be used.

Although the compounds of formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises an indazolone of the formula I, or a pharmaceuticallly acceptable salt thereof, or a (1-4C)alkoxycarbonyl derivative thereof, as defined hereinbefore, in conjunction or admixture with a cyclooxygenase inhibitory non-steroidal anti-inflammatory agent (such as mentioned above), and a pharmaceutically acceptable diluent or carrier.

The cytoprotective effects of the compounds of formula I may be demonstrated, for example in a standard laboratory model which assesses protection against indomethacin induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporations in vacuo and work-up procedures were carried out after removal of residual solids (such as zinc powder) by filtration;

(ii) operations were carried out at room temperature, that is in the range 18-20° and under an atmosphere of an inert gas such as argon;

(iii) column chromatography (by the flash procedure) and medium pressure liquid chromatography (MPLC) were performed on Merck Kieselgel (Art. 9385) obtained from E. Meck, Darmstadt, W. Germany;

(iv) yields are given for illustration only and are not necessarily the maximum attainable;

(v) the end-products of formula I have satisfactory microanalyses and their structure was confirmed by NMR and mass spectral techniques;

(vi) intermediates were not generally fully characterised and purity was assessed by thin layer chromatographic, infra-red (IR) or NMR analysis; and (vii) melting points are uncorrected and were determined using a Koffler block apparatus; melting points for the end-products of formula I were determined after recrystallisation from a conventional organic solvent such as ethanol, methanol, acetone, ether or hexane, alone or in admixture.

EXAMPLE 1

A solution of sodium hydroxide (4.13 g) in water (80 ml) was added to a solution of N-(1-naphthylmethyl)-2-nitrobenzamide (7.6 g) in methanol (60 ml). Zinc powder (3.35 g) was then added to the mixture which was heated under reflux for 24 hours. After cooling, the zinc residue was separated by filtration and the methanol was partially evaporated. The residual solution was then adjusted to pH7 with hydrochloric acid. The precipitated solid was collected, dried and purified by column chromatography, eluting with methylene chloride/ether/methanol (50/50/5 v/v) to give 1,2-dihydro-2-(1-naphthylmethyl)-3H-indazol-3-one (3.0 g), as a white solid after washing with acetone, m.p. 198-200° C. (acetone/ether).

The starting benzamide derivative was obtained as follows:

1-Ethoxycarbonyl-2-ethoxy-1,2-dihydroquinoline (7.5 g), was added in portions to a solution of 2-nitrobenzoic acid (5.01 g) in methylene chloride (300 ml) cooled to 0° C. The mixture (containing ethyl 2-nitrobenzoyl carbonate) was stirred for 15 minutes and then 1-naphthylmethylamine (4.7 g) was added dropwise at 0-5° C. The mixture was then stirred for 1 hour at ambient temperature and then washed successively with M hydrochloric acid, M sodium hydroxide and then with water. The organic phase was dried (MgSO$_4$) and evaporated. The residue was purified by column chromatography, eluting with methylene chloride/ether (80/20 v/v) to give N-(1-naphthylmethyl)-2-nitrobenzamide as a white solid (7.9 g), of satisfactory purity.

EXAMPLES 2-16

Using a similar procedure to that described in Example 1, but starting from N-(3,4-dimethoxybenzyl)-2-nitrobenzamide and heating with zinc dust for 20 hours, extracting the concentrated pH7 reaction mixture with methylene chloride and then chromatographing the dried (MgSO$_4$) extracts, there was obtained 1,2-dihydro-2-(3,4-dimethoxybenzyl-3H-indazol-3-one (Ex. 2) as a solid, m.p. 149-150° C., in 68% yield.

Using a similar modified version of the procedure described in Example 1, but starting from the appropriate N-substituted)-2-nitrobenzamide of formula A (Ra=Rb=H), the following compounds of the formula B (Ra=Rb=H) were obtained:

| Example | A | Q | m.p. (°C.) | reaction* duration (hours) | yield (%) |
|---|---|---|---|---|---|
| 3 | direct link | 3-(nonyloxy)-phenyl | 123–124 | 48 | 25 |
| 4 | —CH(CH$_3$)[S]— (−) (a) | phenyl | 145–146 | 12 | 29 |
| 5 | —CH(CH$_3$)[R]— (+) (b) | phenyl | 145–146 | 12 | 54 |
| 6 | —(CH$_2$)$_3$— | phenyl | 140–141 | 10 | 22 |
| 7 | direct link | 4-(1-methyl-hexyloxy)-phenyl | wax*** | 24 | 13 |
| 8 | —CH$_2$— | 2-furyl | 148–149 | 6 | 43 |
| 9 | direct link | 4-butylphenyl | 157–158 | 10 | 20 |
| 10** | —CH$_2$— | phenyl | 174–175 | 3 | 36 |
| 11 | —CH$_2$— | 3-methoxy-phenyl | 148–150 | 6 | 60 |
| 12 | —CH$_2$— | 2-methoxy-phenyl | 163–164 | 10 | 56 |
| 13 | —(CH$_2$)$_4$— | phenyl | 130–131 | 20 | 43 |
| 14+ | —CH$_2$— | 1-phenylcyclopropyl | 205–206 | 33 | 20 |

*period of reflux with zinc dust; sodium hydroxide and methanol.
**Ex. 10 Ra=5 methyl, Rb=H.
***obtained as a wax; microanalysis, C$_{20}$H$_{24}$N$_2$O$_2$ requires: C, 74.1; H, 7.5; N, 8.5%; found: C, 73.8; H. 7.6; N, 8.5%.
(a) $^{20}[\alpha]_D$ − 188(c. 1.0, ethanol); (b) $^{20}[\alpha]_D$ + 198 (c. 1.0, ethanol)
+ A mixture of ethanol and water (95/5 v/v) was used in place of aqueous methanol as the reaction solvent.

Using a similar modified version of the procedure described in Example 1 there were obtained:

EXAMPLE 15

Starting from N-(allyl)-2-nitrobenzamide and with a reaction duration of 48 hours, 1,2-dihydro-2-allyl-3H-indazol-3-one (Ex. 15)) as a solid, m.p. 110–111° C., in 34% yield.

EXAMPLE 16

Starting from N-(octyl)-2-nitrobenzamide and with a reflux period of 24 hours, 1,2-dihydro-2-octyl-3H-indazol-3-one (Ex. 16) as a solid, m.p. 63–64° C., in 19% yield.

The necessary starting 2-nitrobenzamide derivatives of formula A (Ra=Rb=H) were obtained using similar procedures to those described for the starting materials for Examples 1 and 24, that is by reacting ethyl 2-nitrobenzoyl carbonate or 2-nitrobenzoyl chloride with the appropriate amine of the formula NH$_2$.A.Q, and had the following characteristic properties:

| Starting material for Ex No. | A | Q | m.p. (°C.) |
|---|---|---|---|
| 2 | CH$_2$ | 3,4-dimethoxyphenyl | *** |
| 3 | direct link | 3-(nonyloxy)phenyl | *** |
| 4 | —CH(CH$_3$)— [S] (−) | phenyl | 156–157 |
| 5 | —CH(CH$_3$)— [R] (+) | phenyl | 157–158 |
| 6 | —(CH$_2$)$_3$— | phenyl | 80–82 |
| 7 | direct link | 4-(1-methylhexloxy)-phenyl | *** |
| 8 | —CH$_2$— | 2-furyl | 104–106 |
| 9 | direct link | 4-butylphenyl | *** |
| 10** | —CH$_2$— | phenyl | 156–157 |
| 11 | —CH$_2$— | 3-methoxyphenyl | 96–98 |
| 12 | —CH$_2$— | 2-methoxyphenyl | *** |
| 13 | —(CH$_2$)$_4$— | phenyl | 98–100 |
| 14 | —CH$_2$— | 1-phenylcyclopropyl | 112–113 |
| 15. | | allyl | *** |
| 16 | | octyl | 59–60 |

**Ra=5 methyl, Rb=H.
***Where no melting point is given, the compound was obtained as a solid of satisfactory purity as judged by TLC, IR and/or NMR analysis.

The amine required for Example 14 was obtained by Raney nickel catalysed hydrogenation of 1-phenyl-1-cyclopropanecarbonitrile in methanol using hydrogen at approximately 2.1 bar pressure, and was isolated after column chromatographic purification [using first methylene chloride and then methylene chloride/methanol (80:20 v/v) as eluant] as a yellow oil in 58% yield.

EXAMPLES 17–27

Using a similar procedure to that described in Example 1 the following compounds of formula B (Ra=Rb=H) were obtained:

| Example | A | Q | m.p. (°C.) | reaction* duration (hours) | yield (%) |
|---|---|---|---|---|---|
| 17 | direct link | 4-isopropoxy-phenyl | 186–188 | 24 | 21 |
| 18+++ | direct link | trans-2-phenylcyclopropyl | 130–131 | 48 | 7 |
| 19 | —(CH$_2$)$_2$— | phenyl | 164–165 | 10 | 42 |
| 20 | direct link | 4-butoxyphenyl | wax + | 15 | 10 |
| 21 | direct link | 4-butylthio-phenyl | 156–158 | 72** | 11 |
| 22 | —CH$_2$— | 4-chlorophenyl | 188–190 | 8 | 29 |
| 23 | —CH$_2$— | 2-thienyl | 182–184 | 5** | 45 |
| 24 | —CH$_2$— | 3-pyridyl | 174–175 | 18** (a) | 60 |
| 25 | —CH$_2$— | 2,4-dimethoxy-phenyl | 138–140 | 20** (b) | 46 |

-continued

| Ex-ample | A | Q | m.p. (°C.) | reaction* duration (hours) | yield (%) |
|---|---|---|---|---|---|
| 26*** | direct link | 4-butylphenyl | 220-230 (dec.) | 7 | 14 |
| 27++ | —CH$_2$— | phenyl | 195-205 (dec.) | 1.5 | 53 |

Notes:
*reaction time with zinc dust, sodium hydroxide solution and methanol.
**ethanol used in place of methanol as reaction solvent.
***Ex. 26; Ra=6 chloro, Rb=H.
+ obtained as a waxy solid; microanalysis, C$_{17}$H$_{18}$N$_2$O$_2$ requires: C, 72.3; H, 6.4; N, 9.9%; found: C, 72.3; H, 6.3; N, 9.7%.
++ Ex. 27; Ra=4-fluoro, Rb=H.
+++A mixture of ethanol and water (95/5 v/v) was used in place of aqueous methanol as the reaction solvent.
(a) reaction mixture work-up as in Example 28 below.
(b) reaction mixture work-up as in Example 30 below.

The necessary starting materials of formula A (Ra=Rb=H) were obtained using a similar procedure to that described in Example 1 or using a similar procedure to that described below for the starting material of Example 24:

A mixture of 2-nitrobenzoic acid (5 g) and thionyl chloride (5 ml) was heated under reflux for 30 minutes and then concentrated in vacuo. The residue was dissolved in dry toluene (20 ml) and the volatile material was evaporated. This procedure was repeated. The 2-nitrobenzoyl chloride thus obtained was dissolved in methylene chloride (20 ml). This solution was then added to a solution of 3-(aminomethyl)pyridine (3.24 g) and triethylamine (3.03 g) in methylene chloride (50 ml) at 0° C. After the addition was complete, the reaction mixture was washed with water, dried (MgSO$_4$) and evaporated to give 3-(N-(2-nitrobenzoyl)aminomethyl)-pyridine as a solid of satisfactory purity and in essentially quantitative yield.

The other starting materials of formula A (Ra=Rb=H) had the following characteristic properties:

| Starting material for Ex No. | A | Q | m.p. (°C.) |
|---|---|---|---|
| 17 | direct link | 4-isopropoxyphenyl | + |
| 18 | direct link | trans-2-phenylcyclopropyl | 160-162 |
| 19 | —(CH$_2$)$_2$— | phenyl | 113-114 |
| 20 | direct link | 4-butoxyphenyl | + |
| 21 | direct link | 4-butylthiophenyl | 111-112 |
| 22 | —CH$_2$— | 4-chlorophenyl | + |
| 23 | —CH$_2$— | 2-thienyl | + |
| 25 | —CH$_2$— | 2,4-dimethoxyphenyl | 124-125 |
| 26*** | direct link | 4-butylphenyl | 120-121 |
| 27++ | —CH$_2$— | phenyl | 132-135 |

Notes:
***for Ex. 26; Ra=4-chloro, Rb=H.
++ for Ex. 27; Ra=6-fluoro, Rb=H.
+ obtained as a solid of satisfactory purity for further reaction, as judged by NMR, IR and/or TLC analysis.

EXAMPLE 28

The procedure described in Example 1 was carried out using a reflux period of 4 hours, using N-(4-dimethylaminophenyl)-2-nitrobenzamide (obtained as a solid of satisfactory purity by reaction of 2-nitrobenzoyl chloride with 4-dimethylaminoaniline) as starting material, evaporating the initial reaction mixture to dryness in vacuo, triturating the residue with methylene chloride and methanol (2:1 v/v), evaporating the organic phase and purifying the residue by column chromatography, there was thus obtained 1,2-dihydro-2-(4-dimethylaminophenyl)-3H-indazol-3-one as a solid, m.p. 315-317° C., in 10% yield.

EXAMPLE 29

The procedure described in Example 1 was repeated using N-(4-methylthiophenyl)-2-nitrobenzamide (obtained as a solid of satisfactory purity, by reaction of 2-nitrobenzoyl chloride with 4-methylthioaniline) as starting material, dissolving the precipitate formed at pH7 in a mixture of 2M sodium hydroxide and N,N-dimethylformamide (DMF) (1:1 v/v) and purifying the solution obtained by chromatography on HP20SS polystyrene resin (available from Mitsubishi Chemical Industries), using water and then methanol as eluant. There was thus obtained 1,2-dihydro-2-(4-methylthiophenyl)-3H-indazol-3-one as a solid, m.p. 196-197° C., in 38% yield.

EXAMPLE 30

The procedure described in Example 1 was repeated using N-(1-indanyl)-2-nitrobenzamide (obtained as a solid, m.p. 168-170° C., by reaction of 2-nitrobenzoyl chloride with 1-aminoindan), diluting the reaction mixture with water and then extracting with methylene chloride. The extracts were discarded and the aqueous phase was acidified to pH2 using 2M hydrochloric acid and then extracted with methylene chloride. These extracts were dried (MgSO$_4$) and evaporated. Crystallisation of the residue twice from acetone/ether gave 1,2-dihydro-2-(1-indanyl)-3H-indazol-2-one as a solid, m.p. 187-188° C., in 20% yield.

EXAMPLES 31-33

The procedure described in Example 1 was repeated using N-benzyl-2-nitro-6-methylbenzamide (obtained as a solid, m.p. 139-140° C., from 2-nitro-6-methylbenzoyl chloride and benzylamine) and carrying out the reaction under reflux for 2 hours. The cooled reaction mixture was acidified to pH5 with 2M hydrochloric acid and then extracted with ethyl acetate. These extracts were dried (MgSO$_4$), evaporated and the residue purified by column chromatography, using methylene chloride/ether (90:10 v/v) as eluant, to give 1,2-dihydro-2-benzyl-4-methyl-3H-indazol-3-one (Ex. 31) as a solid, m.p. 151-153° C. (recrystallised from ether/pentane) in 29% yield.

Using a similar procedure, but starting from N-benzyl-5-butoxy-2-nitrobenzamide (obtained as a solid, m.p. 109-110° C., by reaction of 5-butoxy-2-nitrobenzoyl chloride with benzylamine) and using a mixture of ethanol and water (95/5 v/v) in place of aqueous methanol as the reaction solvent, there was obtained 1,2-dihydro-2-benzyl-5-butoxy-3H-indazol-3-one (Ex. 32) as a solid, m.p. 146-147° C., in 7% yield.

Similarly, starting from N-[1(R)-(napth-1-yl)ethyl]-2-nitrobenzamide (obtained as a solid, m.p. 148-150° C., by reaction of 2-nitrobenzoyl chloride with (+)-1(R)-(napth-1-yl)ethylamine), there was obtained 1,2-dihydro-2-[1(R)-napth-1-yl)ethyl]-3H-indazol-3-one (Ex. 33) as a solid, m.p. 232-233° C., in 25% yield; $^{20}[\alpha]_D$ +166.5 (c1.0,methanol).

EXAMPLE 34

The procedure described in Example 1, was repeated using N-[4-(1-hydroxypentyl)benzyl]-2-nitrobenzamide (obtained as a solid, m.p. 94–96° C. by reaction of 2-nitrobenzoyl chloride with 4-(1-hydroxypentyl)benzylamine), using a mixture of ethanol and water (95/5 v/v) in place of aqueous methanol as the reaction solvent, carrying out the reaction under reflux for 5 hours and using a mixture of methylene chloride/ethyl acetate/ethanol (180:60:10 v/v) as eluant in the chromatographic purification stage. There was thus obtained 1,2-dihydro-2-[4-(1-hydroxypentyl)benzyl]-3H-indazol-3-one as a solid, m.p. 110–114° C., in 45% yield.

The starting 4-(1-hydroxypentyl)benzylamine was obtained as follows:

A solution of butyllithium in hexane (5 ml of 1.6M solution) was added during 1 hour to a stirred solution of 4-cyanobenzaldehyde (1.05 g) in dry tetrahydrofuran (THF) (40 ml) cooled to −78° C. and maintained under an atmosphere of argon. The reaction was then quenched by careful addition of saturated aqueous ammonium chloride solution (30 ml) and extracted with ether (3×10 ml). The extracts were dried (MgSO$_4$) and evaporated. The residue was dissolved in methylene chloride and purified by filtration through chromatographic silica gel. The solid obtained (0.5 g) (which contained 7:1 parts of 4-(1-hydroxypentyl)benzonitrile and butyl 4-(1-hydroxypentyl)phenyl ketone, respectively as judged by NMR spectral analysis) was dissolved in ether (20 ml). The solution was heated under reflux with lithium aluminium hydride (0.3 g) for 4 hours. Excess hydride was decomposed by addition of ethyl acetate (5 ml) and then water (5 ml). The precipitate was separated by filtration and washed with ethyl acetate/methanol (80:20 v/v). The combined filtrate and washings were dried (MgSO$_4$) and evaporated. A solution of the residue in ether was treated with a saturated solution of hydrogen chloride in ether to give 4-(1-hydroxypentyl)benzylamine hydrochloride (0.325 g) as a white solid, m.p. 172–173° C. An ethereal solution of the free base was obtained in situ by treating the hydrochloride with aqueous sodium hydroxide and ether in a conventional manner.

EXAMPLE 35

A mixture of 1,2-dihydro-1-carboethoxy-3H-indazol-3-one (G. Heller and P. Jacobsohn, Chem. Ber, 1921, 54B, 1107; 2.06 g), triethylamine (1.01 g) and bromodiphenylmethane (2.5 g) in chloroform (60 ml) was heated under reflux for 4 hours. The reaction mixture was then washed successively with water, M hydrochloric acid and then with water, dried (MgSO$_4$) and evaporated. The residue was dissolved in methylene chloride and purified by column chromatography using an increasing gradient of ether in methylene chloride as eluant to give (from the later fractions) 1,2-dihydro-1-carboethoxy-2-diphenylmethyl-3H-indazol-3-one as a solid (1.4 g), m.p. 115–118° C.

EXAMPLE 36

A solution of 1,2-dihydro-1-carboethoxy-2-diphenylmethyl-3H-indazol-3-one (1.4 g) in ethanol (15 ml) containing potassium hydroxide (820 mg) was heated at 80° C. for 30 minutes. The reaction mixture was diluted with water (50 ml) and extracted with ether. The extracts were discarded. The aqueous phase was acidified to pH2 with 2M hydrochloric acid and extracted with methylene chloride. These extracts were dried (MgSO$_4$) and evaporated. The residue was recrystallised from acetone/ether to give 1,2-dihydro-2-diphenylmethyl-3H-indazol-3-one as a solid (0.6 g), m.p. 179–181° C.

EXAMPLE 37

Using a similar alkylation procedure to that described in Example 35, but using chloromethyl phenyl sulphide instead of bromodiphenylmethane, there was obtained 1,2-dihydro-1-carboethoxy-2-phenylthiomethyl-3H-indazol-3-one as a solid m.p. 87–88° C., 73% yield.

EXAMPLE 38

Using a similar hydrolysis procedure to that described in Example 36, there was obtained 1,2-dihydro-2-phenylthiomethyl-3H-indazol-3-one as a solid, m.p. 167–168° C., in 63% yield starting from the corresponding 1-carboethoxy derivative.

EXAMPLES 39–40

4-Nitrobenzyl bromide (540 mg) was added to a mixture of 1,2-dihydro-1-carboethoxy-3H-indazol-3-one (206 mg) and potassium hydroxide (67 mg) in ethanol (10 ml). The mixture was heated under reflux for 30 minutes. The cooled solution was clarified by filtration and the filtrate was evaporated. The residue was purified by column chromatography using methylene chloride as eluant to give 1,2-dihydro-1-carboethoxy-2-(4-nitrobenzyl)-3H-indazol-3-one (Ex. 39) as a solid, m.p. 123–124° C. in 59% yield.

Using a similar alkylation procedure, but employing 2-(bromomethyl)naphthalene as the alkylating agent, there was obtained 1,2-dihydro-1-carboethoxy-2-(2-naphthylmethyl)-3H-indazol-3-one (Ex. 40) as a solid, in 64% yield, having a satisfactory NMR and microanalysis.

EXAMPLES 41–42

Using a similar hydrolysis procedure to that described in Ex. 36, there was obtained:
(Example 41): 1,2-dihydro-2-(4-nitrobenzyl)-3H-indazol-3-one as a solid, m.p. 198–200° C., in 26% yield; and
(Example 42): 1,2-dihydro-2-(2-naphthylmethyl)-3H-indazol-3-one, as a solid, m.p. 208–212° C. (recrystallised from acetone), in 85% yield;
in both cases, starting from the corresponding 1-carboethoxy derivative.

EXAMPLES 43–44

N-(Benzyl)-4-chloro-2-nitrobenzamide (obtained by reaction of benzylamine with 4-chloro-2-nitrobenzoyl chloride) (1.16 g) was dissolved in a mixture of methanol (20 ml) and water (4 ml). Zinc dust (520 mg) was then added in one portion. Ammonium acetate (1.23 g) was then added in portions to the rapidly stirred reaction mixture. After the addition was complete, 2M sodium hydroxide solution (8 ml) was added and the mixture was heated under reflux for 4 hours. The cooled mixture was then concentrated in vacuo to remove methanol and then acidified to pH6 with 2M hydrochloric acid. This mixture was extracted with ethyl acetate. The extracts were washed with brine, dried (MgSO$_4$) and evaporated. The residue was purified by column chromatography using an increasing gradient of ether in methylene chloride to give 1,2-dihydro-2-benzyl-6- chloro-3H-indazol-3-one (Ex. 43) as a solid (0.2 g), m.p. 209-214° C.

Using an analogous procedure, but starting from N-(2-fluorophenyl)-4-chloro-2-nitrobenzamide (obtained by reaction of 2-fluoroaniline with 4-chloro-2-nitrobenzoyl chloride), there was obtained 1,2-dihydro-6-chloro-2-(2-fluorophenyl)-3H-indazol-3-one (Ex. 44) as a solid, m.p. 205-215° C. in 30% yield.

EXAMPLE 45

A suspension of 2-(2-benzylhydrazino)-5-chlorobenzoic acid (2.5 g) in acetic acid (20 ml) was heated under reflux for 30 minutes. The solution was then cooled and diluted with ether. The solid which formed was recrystallised from ethanol to give 1,2-dihydro-2-benzyl-5-chloro-3H-indazol-3-one as a solid (1.6 g), m.p. 215-225° C. (dec.).

The necessary starting material was obtained as follows:

(i) A solution of benzaldehyde (1.48 g) in ethanol (10 ml) was added to a stirred suspension of 5-chloro-2-hydrazinobenzoic acid hydrochloride (described in U.S. Pat. No. 4,105,766; 5.2 g) in water (100 ml). Stirring was continued for 1 hour. The mixture was then left unstirred for 16 hours and then extracted with ether. The extracts were dried (MgSO4) and evaporated to give 2-(benzylidenehydrazino)-5-chlorobenzoic acid (3.5 g) which was used without purification.

(ii) A solution of sodium cyanoborohydride (780 mg) in methanol (20 ml) was added to a stirred solution of 2-(benzylidenehydrazino)-5-chlorobenzoic acid (2.7 g) in THF (20 ml) containing a few milligrams of the indicator Congo Red. A methanolic solution of hydrogen chloride was added dropwise until the indicator in the reaction solution turned blue. Stirring was continued for 15 minutes. The reaction mixture was diluted with water and extracted with ethyl acetate. The extracts were washed with brine, dried (MgSO4) and evaporated to give 2-(2-benzylhydrazino)-5-chlorobenzoic acid as a solid (2.5 g) which was used without purification.

EXAMPLE 46

A stirred suspension of 2-(2-fluorobenzoyl)aniline (4.3 g) in 5M hydrochloric acid (28 ml) was diazotised at 0-5° C. by addition of an ice-cold solution of sodium nitrite (2.76 g) in water (8 ml). After the addition was complete, stirring was continued at 0-5° C. for 20 minutes. The yellow solution obtained was added dropwise to a rapidly stirred solution of sodium sulphite (3.78 g) in water (15 ml). Stirring was continued for 45 minutes. The solid which formed was collected by filtration and heated with aqueous sodium hydroxide solution (2% w/v. 150 ml) for 2 hours at 100° C. The cooled mixture was extracted with ethyl acetate. The aqueous phase was acidified to pH2 with 2M hydrochloric acid and extracted with ethyl acetate. The combined ethyl acetate phases were washed with brine, dried (MgSO4) and evaporated. The residue was purified by column chromatography using methylene chloride/ether (90:10 v/v) as eluant to give 1,2-dihydro-2-(2-fluorophenyl)-3H-indazol-3-one as a solid (260 mg), m.p. 156-159° C.

EXAMPLE 47

Using a similar procedure to that described in Example 46, but starting from 5-bromo-2-(2-fluorobenzoyl)aniline, there was obtained 1,2-dihydro-5-bromo-2-(2-fluorophenyl)-3H-indazol-3-one as a solid, m.p. 200-205° C. in 2% yield.

EXAMPLES 48-51

Boron tribromide (0.6 ml) was added dropwise to a stirred suspension of 1,2-dihydro-2-(4-methoxyphenyl)-3H-indazol-3-one (Ardakani et alia, Tet. Letters, 1979, 29,4765) (0.48 g) in methylene chloride at −80° C. After the addition was complete, the stirred reaction mixture was allowed to reach room temperature and stirring was continued for 4 hours. Water (2 ml) was added and the mixture was then evaporated to dryness. The residue was purified by column chromatography using methylene chloride/ether/methanol (50:50:5 v/v) as eluant to give 1,2-dihydro-2-(4-hydroxyphenyl)-3H-indazol-3-one (Ex. 48) as a solid (0.37 g), m.p. 217-221° C. (dec.) (after recrystallisation from acetone).

Using an analogous procedure, the following hydroxy compounds were made by demethylation of the corresponding methoxy compounds:

(Example 49): 1,2-dihydro-2-(4-hydroxybenzyl)-3H-indazol-3-one as a solid, m.p. 198-203° C. (recrystallised from acetone) in 50% yield;

(Example 50): 1,2-dihydro-2-(3-hydroxybenzyl)-3H-indazol-3-one as a solid, m.p. 185-188° C., in 66% yield; and (Example 51): 1,2-dihydro-2-(2-hydroxybenzyl)-3H-indazol-3-one as a solid, m.p. 215-216° C., in 64% yield.

EXAMPLES 52-53

3-Chloroperbenzoic acid (150mg) was added to a stirred solution of 1,2-dihydro-2-(4-butylthiophenyl)-3H-indazol-3-one (250 mg) in methylene chloride (5 ml) at 0-5° C. Stirring was continued for 15 minutes after the addition was complete. The reaction mixture was then washed with water, dried (MgSO4) and evaporated in vacuo. The residue was purified by column chromatography using methylene chloride/ether (70:30 v/v) to give 1,2-dihydro-2-(4-butylsulphinylphenyl)-3H-indazol-3-one (Ex. 52) as a solid (160 mg), m.p. 168-169° C.

Using a similar procedure, but starting from 1,2-dihydro-2-(4-methylthiophenyl)-3H-indazol-3-one, there was obtained 1,2-dihydro-2-(4-methylsulphinylphenyl)-3H-indazol-3-one (Ex. 53) as a solid, m.p. 208-210° C., in 75% yield.

EXAMPLE 54

Using an analogous procedure to that described in Example 52, but using two molecular equivalents instead of one of 3-chloroperbenzoic acid, there was obtained, 1,2-dihydro-2-(4-butylsulphonylphenyl)-3H-indazol-3-one as a solid, m.p. 209-210° C. in 27% yield.

EXAMPLES 55-57

Using a similar procedure to that described in Example 1, but starting from the appropriate N-substituted-2-nitrobenzamide of formula A (Ra=Rb=H), the following compounds of formula B (Ra=Rb=H), were obtained:

| Example | A | Q | m.p. (°C.) | Reaction* duration | Yield (%) |
|---|---|---|---|---|---|
| 55$^a$ | —CH$_2$— | 4-tolyl | 179-180 | 10 | 68 |
| 56 | m- | (2- | 163-167 | 24 | 7 |

-continued

| Example | A | Q | m.p. (°C.) | Reaction* duration | Yield (%) |
|---|---|---|---|---|---|
| | phenylene | quinolyl)-methoxy | | | |
| 57 | m-phenylene | (2-naphthyl)-methoxy | 193-195 | 8 | 58 |

Notes
*reaction time with zinc dust and sodium hydroxide but using a mixture of ethanol and water (95/5 v/v) in place of aqueous methanol as the reaction solvent.
a.The reaction solvent was a mixture of ethanol and water (13/1 v/v) and the reaction mixture was acidified to pH5.

The necessary starting 2-nitrobenzamide derivatives of formula A (Ra=Rb=H) were obtained using similar procedures to those described for the starting materials for Examples 1 and 24, that is by reacting ethyl 2-nitrobenzoyl carbonate or 2-nitrobenzoyl chloride with the appropriate amine of the formula $H_2N$—A—Q, and had the following characteristic properties:

| Starting material for Ex. No. | A | Q | m.p. (°C.) |
|---|---|---|---|
| 55 | —$CH_2$— | 4-tolyl | 147-148 |
| 56a | m-phenylene | (2-quinolyl)methoxy | 170-171 |
| 57b | m-phenylene | (2-naphthyl)methoxy | 146 |

Notes
a.The required aniline, 3-(2-quinolyl)methoxyaniline is described in J.Med.Chem., 1986, 29, 1429.
b.The required aniline, 3-(2-naphthyl)methoxyaniline is described in J.Med.Chem., 1986, 29, 1429.

EXAMPLES 58-72

Using a similar procedure to that described in Examples 2-16, but starting from the appropriate N-substituted-2-nitrobenzamide of formula A (Ra=Rb=H), the following compounds of formula B (Ra=Rb=H) were obtained:

| Example | A | Q | m.p. (°C.) | reaction* duration (hours) | Yield (%) |
|---|---|---|---|---|---|
| 58 | —$CH_2$— | 4-pyridyl | 140-142 | 6 | 21 |
| 59 | —$CH_2$— | 2-benzimidazol-yl | 226-228 | 72 | 39 |
| 60 | —CH($CH_3$)[RS]— | 3-pyridyl | 161-163 | 4 | 39 |
| 61 | —CH($CH_3$)[RS]— | 2,4-dimethyl-thiazol-5-yl | 134-136 | 4 | 19 |
| 62 | —$CH_2$— | cyclohexyl | 139-141 | 10 | 32 |
| 63+ | —$CH_2$— | 2-tolyl | 179-180 | 0.5 | 60 |
| 64 | —$CH_2$— | 4-butoxyphenyl | 155-156 | 48 | 20 |
| 65 | —$CH_2$— | 3,4-methylenedioxyphenyl | 206-209 | 10 | 67 |
| 66 | —$CH_2$— | 4-hydroxymethyl-phenyl | 158-160 | 6 | 45 |
| 67 | —$CH_2$— | 3-chlorophenyl | 161-164 | 4 | 11 |
| 68 | —$CH_2$— | 4-dimethyl-amino-phenyl | 184-186 | 20 | 60 |
| 69 | direct link | 1-phenyl-cyclopropyl | 207 | 7 | 24 |
| 70 | direct link | 1-benzyl-cyclopropyl | 209-217 | 7 | 42 |
| 71 | —($CH_2$)$_2$— | phenyl-amino | 134-135 | 4 | 28 |
| 72** | —$CH_2$— | phenyl | 172-178 | 4 | 7 |

Notes
*Reaction time with zinc dust and sodium hydroxide but using a mixture of ethanol and water (95/5 v/v) in place of aqueous methanol as the reaction solvent.
+The reaction solvent was a mixture of ethanol and water (13/1 v/v)
**Ra = 4-butoxy, Rb = H The necessary starting 2-nitrobenzamide derivatives of formula A (Ra=Rb=H) were obtained using similar procedures to those described for the starting materials for Examples 1 and 24, that is by reacting ethyl 2-nitrobenzoyl carbonate or 2-nitrobenzoyl chloride with the appropriate amine of the formula $H_2N$—A—Q, and had the following characteristic properties:

| Starting material for Ex. No. | A | Q | m.p. (°C.) |
|---|---|---|---|
| 58 | —$CH_2$— | 4-pyridyl | 148-150 |
| 59a | —$CH_2$— | 2-benzimidazolyl | 230-233 |
| 60 | —CH($CH_3$)[RS]— | 3-pyridyl | 145 |
| 61b | —CH($CH_3$)[RS]— | 2,4-dimethylthiazol-5-yl | 162-164 |
| 62 | —$CH_2$— | cyclohexyl | 115-120 |
| 63 | —$CH_2$— | 2-tolyl | 151-152 |
| 64c | —$CH_2$— | 4-butoxyphenyl | 101-102 |
| 65 | —$CH_2$— | 3,4-methylenedioxyphenyl | 127-128 |
| 66d | —$CH_2$— | 4-hydroxymethyl-phenyl | 149 |
| 67 | —$CH_2$— | 3-chlorophenyl | 97-99 |
| 68 | —$CH_2$— | 4-dimethylamino-phenyl | 136-138 |
| 69 | direct link | 1-phenylcyclopropyl | *** |
| 70 | direct link | 1-benzylcyclopropyl | 149-150 |
| 71 | —($CH_2$)$_2$— | phenylamino | *** |
| 72e | —$CH_2$— | phenyl | *** |

Notes
***Where no melting point is given the compound was obtained as a solid of satisfactory purity as judged by TLC, IR and/or NMR analysis.

a. The product crystallised out from the reaction mixture. It was filtered off, washed with water and dried.
b. 5-(1-Aminoethyl)-2,4-dimethylthiazole was prepared as follows:

A solution of 5-acetyl-2,4-dimethylthiazole (4.65 g), hydroxylamine hydrochloride (1.25 g) and sodium acetate trihydrate (2.5 g) in aqueous ethanol (15 ml) was heated to reflux for 1 hour. The solution was allowed to cool overnight and the deposited solid (2.5 g) was filtered off. A mixture of this solid, zinc dust (20 g), ethanol (25 ml) and glacial acetic acid (20 ml) was stirred overnight at ambient temperature, filtered and evaporated. The residue was partitioned between ethyl acetate and dilute aqueous potassium hydroxide solution. The organic solution was dried (MgSO$_4$) evaporated to give the required amine (1.6 g) as an oil of satisfactory purity.

c. N-(4-Butoxybenzyl)-2-nitrobenzamide was prepared as follows:

2-Nitrobenzoyl chloride was reacted with 4-methoxybenzylamine using the procedure described for the preparation of starting materials in Example 24. A mixture of the N-(4-methoxybenzyl)-2-nitrobenzamide (2.84 g) so obtained, a solid with m.p. 127–128° C., and methylene chloride (50 ml) was cooled to −78° C. and boron tribromide (2 ml) was added. The mixture was stirred and allowed to warm to ambient temperature. After 4 hours methanol (5 ml) was added, the mixture was evaporated to dryness and the residue was purified by column chromatography eluting with methylene chloride/diethyl ether (1/1 v/v). There was thus obtained N-(4-hydroxybenzyl)-2-nitrobenzamide as a solid of satisfactory purity. A mixture of this product, potassium carbonate (310 mg), butyl iodide (828 mg) and N,N-dimethylformamide (5 ml) was heated to 100° C. for 15 hours. Further portions of potassium carbonate (155 mg) and butyl iodide (414 mg) were added and heating was continued for a further 10 hours. The solvent was evaporated, the residue was triturated in methylene chloride and the organic solution was evaporated to dryness. The residue was purified by column chromatography eluting with methylene chloride. There was thus obtained N-(4-butoxybenzyl)-2-nitrobenzamide as a solid (0.81 g), m.p. 101–102° C., in 58% yield.

d. The amine starting material was obtained by reduction of a solution of 4-cyanobenzaldehyde in diethyl ether with lithium aluminium hydride.

e. Ra=4-butoxy, Rb=H. 2-Butoxy-6-nitrobenzoyl chloride was prepared by the reaction of thionyl chloride and the corresponding benzoic acid which, in turn, was prepared by hydrolysis of the corresponding butyl ester with sodium hydroxide in aqueous ethanol. The butyl ester was prepared by heating together a mixture containing 2-hydroxy-6-nitrobenzoic acid (Chem.Abs., 1963, 59, 500 g), butyl iodide, potassium carbonate and N,N-dimethylformamide.

EXAMPLE 73

The procedure described in Example 30 was repeated using N-[3-(1-hydroxyhexyl)benzyl]-2-nitrobenzamide (obtained as a solid, m.p. 116–118° C., by reaction of 2-nitrobenzoyl chloride and 3-(1-hydroxyhexyl)benzylamine, the latter having been prepared by reacting 3-cyanobenzaldehyde with pentyl magnesium bromide and by reducing the product, 3-(1-hydroxyhexyl)-benzonitrile, with lithium aluminium hydride) as starting material but with a reaction duration of 7 hours and using ethanol/water (3/1 v/v) as solvent. There was thus obtained 1,2-dihydro-2-[3-(1-hydroxyhexyl)benzyl]-3H-indazol-3-one as a solid, m.p. 125–127° C. (recrystallised from methylene chloride/diethyl ether), in 63% yield.

EXAMPLE 74

The procedure described in Example 28 was repeated using N-(2,3-dimethoxybenzyl)-2-nitrobenzamide (obtained as a solid, m.p. 128–129° C., by reaction of 2-nitrobenzoyl chloride with 2,3-dimethoxybenzylamine) as starting material but with a reaction duration of 18 hours and using a mixture of ethanol and water (13/1 v/v) as the solvent. There was thus obtained 1,2-dihydro-2-(2,3-dimethoxybenzyl)-3H-indazol-3-one as a solid, m.p. 78–79° C. (recrystallised from aqueous ethanol), in 47% yield.

EXAMPLES 75–81

Using a similar procedure to that described in Examples 31–33, but starting from the appropriate N-substituted-2-nitrobenzamide of formula A (Ra=Rb=H), the following compounds of formula B (Ra=Rb=H) were obtained:

| Example | A | Q | m.p. (°C.) | reaction* duration (hours) | Yield (%) |
|---|---|---|---|---|---|
| 75 | —CH$_2$— | 3-(1-hydroxypropyl)-phenyl | 127 | 15 | 18 |
| 76$^a$ | —CH(CH$_3$)—[S](—) | 1-naphthyl | 230–232 | 36 | 30 |
| 77 | —(CH$_2$)$_2$— | 2-pyridyl | 103–104 | 3 | 63 |
| 78 | direct link | 4-chromanyl | 249 | 5 | 42 |
| 79 | direct link | 1-tetrahydronaphthyl | 210–212 | 14 | 43 |
| 80 | —CH$_2$— | t-butyl | 208–209 | 7 | 57 |
| 81$^b$ | —(CH$_2$)$_2$— | morpholino | 150 | 8 | 49 |

Notes
*period of reflux with zinc dust and sodium hydroxide but using a mixture of ethanol and water (95/5 v/v), in place of aqueous methanol, as the reaction solvent. The following work up was used: - the cooled reaction mixture was evaporated to remove the bulk of the ethanol, diluted with water (20 ml), washed with diethyl ether and acidified to pH5 with 2 M hydrochloric acid and extracted with ethyl acetate.
$^{a.20}[α]_D$ − 154.8 (c 1.1, methanol).
$^b$The reaction mixture was acidified to pH7 prior to extraction with ethyl acetate.

The necessary starting 2-nitrobenzamide derivatives of formula A (Ra=Rb=H) were obtained using similar procedures to those described for the starting materials for Examples 1 and 24, that is by reacting ethyl 2-nitrobenzoyl carbonate or 2-nitrobenzoyl chloride with the appropriate amine of the formula H$_2$N—A—Q, and had the following characteristic properties:

| Starting material for Ex. No. | A | Q | m.p. (°C.) |
|---|---|---|---|
| 75$^a$ | —CH$_2$— | 3-(1-hydroxypropyl)-phenyl | *** |
| 76 | —CH(CH$_3$)—[S](—) | 1-naphthyl | *** |
| 77 | —(CH$_2$)$_2$— | 2-pyridyl | 106 |
| 78$^b$ | direct link | 4-chromanyl | 192 |
| 79 | direct link | 1-tetrahydronaphthyl | 167 |
| 80 | —CH$_2$— | t-butyl | *** |
| 81 | —(CH$_2$)$_2$— | morpholino | 118 |

Notes
***Where no melting point is given, the compound was obtained as a solid of satisfactory purity as judged by TLC, IR and/or NMR analysis.
$^a$The amine starting material was obtained by reacting 3-cyanobenzaldehyde with ethyl magnesium bromide and by reducing the product, 3-(1-hydroxypropyl)-benzonitrile, with lithium aluminium hydride.
$^b$The amine starting material is described in Chem.Abs., 1978, 90, 87194w

EXAMPLE 82

Using a similar procedure to that described in Example 34, but starting from N-benzyl-4-butoxy-2-nitrobenzamide [obtained as an oil of satisfactory purity by heating a mixture containing 4-hydroxy-2-nitrobenzoic acid (J.Chem.Soc., 1949, 1502), butyl iodide, potassium carbonate and N,N-dimethylformamide; hydrolysing a solution of the ester in ethanol with aqueous sodium hydroxide and coupling the resultant acid with benzylamine using the conditions described for the preparation of starting materials in Example 1], using a mixture of ethanol and water (3/1 v/v) as solvent and heating the reaction for 8 hours there was obtained 1,2-dihydro-2-benzyl-6-butoxy-3H-indazol-3-one as a solid, m.p. 148–149° C., in 27% yield.

EXAMPLES 83–97

Using a similar alkylation procedure to that described in Example 35, but using the appropriate alkyl bromide instead of bromodiphenylmethane, there were obtained the following compounds of formula C (Ra=Rb=H; Rd=CO$_2$Et):

| Example | A | Q | m.p.* (°C.) | reaction duration (hours) | yield (%) |
|---|---|---|---|---|---|
| 83$^a$ | —CH$_2$— | 2-pyridyl | 97 | 72 | 20 |
| 84$^b$ | —CH$_2$— | 2-chloropyrid-3-yl | 64 | 4 | 37 |
| 85$^c$ | —CH$_2$— | 2-methoxypyrid-5-yl | 95–98 | 4 | 28 |
| 86 | —CH$_2$— | m-tolyl | oil | 4 | 24 |
| 87$^d$ | —CH$_2$— | 3-fluorophenyl | 87 | 4 | 41 |
| 88 | —CH$_2$— | 3-bromophenyl | oil | 4 | 60 |
| 89 | —CH$_2$— | 2-bromophenyl | 64–65 | 21 | 37 |
| 90 | —CH$_2$— | 3-nitrophenyl | oil | 4 | 68 |
| 91 | —CH$_2$— | 4-cyanophenyl | 94–95 | 4 | 68 |
| 92 | —CH$_2$— | 3-cyanophenyl | oil | 4 | 37 |
| 93$^e$ | —CH$_2$— | 4-biphenyl | 103–105 | 20 | 47 |
| 94$^f$ | —CH$_2$— | 3-biphenyl | oil | 5 | 23 |
| 95$^g$ | —CH$_2$— | benzyloxy | oil | 0.16 | 61 |
| 96$^h$ | —CH$_2$— | cyano | oil | 3 | 68 |
| 97$^i$ | —CH$_2$— | 2-chloropyrid-5-yl | 89–90 | 7 | 34 |

Notes
*Where the product was obtained as an oil it was shown to be of satisfactory purity as judged by TLC, IR and/or NMR analysis.
$^a$2-Chloromethylpyridine was used in place of the corresponding 2-bromomethyl compound. During the work-up the wash with M hydrochloric acid was omitted.
$^b$2-Chloro-3-chloromethylpyridine used in place of the corresponding 3-bromomethyl compound was prepared from 2-chloronicotinic acid using the route described in J. Org Chem., 1969, 34, 3545, to prepare 2-chloro-3-hydroxymethylpyridine. A solution of this alcohol (5 g) in toluene (40 ml) was cooled to 0° C., thionyl chloride (3.3 ml) was added and the mixture was stirred for 16 hours at ambient temperature. The mixture was evaporated to give the chloromethyl product as a hydrochloride salt (5 g) of satisfactory purity.
$^c$5-Chloromethyl-2-methoxypyridine, used in place of the corresponding alkyl bromide, was prepared as a hydrochloride salt of satisfactory purity from 5-hydroxymethyl-2-methoxypyridine (Helv, Chim. Acta, 1976, 59, 219) on treatment with thionyl chloride using the procedure described in Note $^b$ above.
$^d$3-Fluorobenzyl iodide (obtained by the reaction of a solution of the corresponding chloride in acetone with sodium iodide) was used in place of the corresponding alkyl bromide.
$^e$p-Phenylbenzyl chloride was used in place of the corresponding alkyl bromide.
$^f$m-Phenylbenzyl bromide was prepared by heating to reflux a mixture of m-phenyltoluene and N-bromosuccinimide in carbon tetrachloride, using irradiation from a 250 Watt lamp to initiate the reaction.
$^g$Benzyl chloromethyl ether was used in place of the corresponding alkyl bromide and the reaction was carried out at ambient temperature.
$^h$Sodium iodide (99 mg) was added to the reaction mixture.
$^i$2-Chloro-5-chloromethylpyridine was prepared as a hydrochloride salt of satisfactory purity by the reaction of 2-chloro-5-hydroxymethylpyridine (J. Org. Chem., 1969, 34, 3545) and thionyl chloride.

EXAMPLES 98–107

Using a similar alkylation procedure to that described in Examples 39–40, but using the appropriate alkyl chloride rather than an alkyl bromide, there were obtained the following compounds of formula C (Ra=Rb=H; Rd=CO$_2$Et):

| Example | A | Q | m.p.* (°C.) | reaction duration (hours) | yield (%) |
|---|---|---|---|---|---|
| 98$^a$ | —CH$_2$— | 2-methylpyrid-5-yl | oil | 0.5 | 37 |
| 99$^b$ | —CH$_2$— | 3-methylpyrid-5-yl | oil | 1 | 20 |
| 100$^c$ | —CH$_2$— | 2-methylpyrid-3-yl | oil | 0.5 | 25 |
| 101$^d$ | —CH$_2$— | 3-bromopyrid-5-yl | 130–133 | 0.75 | 33 |
| 102$^e$ | —CH$_2$— | 6-(4-chlorophenyl)-2-methylpyrid-3-yl | oil | 0.5 | 25 |
| 103$^f$ | —CH$_2$— | 4-methylthiazol-5-yl | oil | 1 | 43 |
| 104$^g$ | —CH$_2$— | 2,4-dimethylthiazol-5-yl | oil | 0.5 | 16 |
| 105$^h$ | —CH$_2$— | 3-trifluoromethylphenyl | oil | 0.75 | 76 |
| 106$^i$ | —CH$_2$— | pyrazinyl | oil | 0.5 | 17 |
| 107$^j$ | —CH$_2$— | 5-thiazolyl | oil | 0.5 | 22 |

Notes
*Where the product was obtained as an oil, it was shown to be of satisfactory purity as judged by TLC, IR and/or NMR analysis.
$^a$5-Chloromethyl-2-methylpyridine was prepared as a hydrochloride salt of satisfactory purity by the reaction of 5-hydroxymethyl-2-methylpyridine (Chem. Abs., 1958, 52, 18399 g) and thionyl chloride.
$^b$Bromomethyl-5-methylpyridine, used in place of the corresponding chloride, was prepared by the reaction of a solution of 3,5-lutidine in carbon tetrachloride with N-bromosuccinimide. The solution was cooled and filtered and the filtrate was used directly in the alkylation reaction.
$^c$3-Chloromethyl-2-methylpyridine is described in Chem. Pharm. Bull. 1959, 7, 241.
$^d$3-Bromo-5-iodomethylpyridine was prepared as an oil of satisfactory purity by the reaction of a solution of 3-bromo-5-chloromethylpyridine (described in Chem. Ber., 1973, 106, 223) in acetone with sodium iodide. This iodide was used in place of the corresponding alkyl chloride.
$^e$3-Chloromethyl-6-(4-chlorophenyl)-2-methylpyridine was prepared as an oil of satisfactory purity from ethyl 6-(4-chlorophenyl)-2-methylnicotinate (Chem. Abs., 1960, 54, 8815e) using the method, described in Chem. Abs. 1969, 71, 38813w, of reduction with lithium aluminium hydride and chlorination with thionyl chloride.
$^f$5-Chloromethyl-4-methylthiazole was prepared as an oil of satisfactory purity from methyl 4-methylthiazole-5-carboxylate (J. Amer. Chem. Soc., 1939, 61, 891) using the method, described in Note $^e$ above.
$^g$5-Chloromethyl-2,4-dimethylthiazole was prepared as an oil of satisfactory purity from ethyl 2,4-dimethylthiazole-5-carboxylate (Chem. Abs., 1946, 40, 4056) using the method described in Note $^e$ above.
$^h$3-Trifluoromethylbenzyl iodide, used in place of the corresponding chloride, was prepared as an oil of satisfactory purity by the reaction of a solution of the corresponding benzyl chloride in acetone with sodium iodide.
$^i$2-Iodomethylpyrazine, used in place of the corresponding chloride, was prepared by the reaction of a solution of the chloride (J. Org. Chem., 1973, 38, 2051) in acetone with sodium iodide.
$^j$5-Chloromethylthiazole is described in J. Med. Chem., 1973, 16, 978.

EXAMPLES 108–110

A mixture of 1,2-dihydro-1-carboethoxy-3H-indazol-3-one (5 g), 2-chloromethylquinoline hydrochloride (5.35 g), caesium carbonate (23.6 g), caesium iodide (100 mg) and acetone (1 l) was stirred under an atmosphere of argon and heated to reflux for 7 hours. The mixture was filtered and the filtrate was evaporated. The residue was purified by column chromatography using methylene chloride/ethyl acetate (50/3 v/v) as eluant. There was thus obtained 1,2-dihydro-1-carboethoxy-2-(2-quinolylmethyl)-3H-indazol-3-one (Ex. 108) as a solid (2.15 g), m.p. 119–120° C., in 25% yield.

Using a similar alkylation procedure, but employing cyclohex-2-en-1-yl bromide as the alkylating agent, using potassium carbonate in place of caesium carbonate and caesium iodide, using N,N-dimethylformamide as the solvent and carrying out the reaction at ambient temperature for 3 hours, there was obtained 1,2-dihydro-1-carboethoxy-2-(cyclohex-2-en-1-yl)-3H-indazol-3-one (Ex. 109) as an oil of satisfactory purity in 33% yield.

Using a similar alkylation procedure, but employing 2-methylprop-2-en-1-yl chloride as the alkylating agent, using potassium carbonate as the base, using N,N-dimethylformamide as the solvent and carrying out the reaction at 40° C. for 10 hours, there was obtained 1,2-dihydro-1-carboethoxy-2-(2-methylprop-2-en-1-yl)-3H-indazol-3-one (Ex. 110) as a solid, m.p. 48–50° C., in 62% yield.

EXAMPLES 111–142

A mixture of 1,2-dihydro-1-carboethoxy-2-[(4-methylthiazol-5-yl)methyl]-3H-indazol-3-one (5 g), powdered potassium hydroxide (4.4 g) and ethanol (100 ml) was heated to reflux for 30 minutes. The mixture was cooled in an ice-bath and acidified to pH5 with acetic acid. The bulk of the ethanol was evaporated and the residue was partitioned between methylene chloride and water. The organic solution was dried (MgSO₄) and evaporated to give 1,2-dihydro-2[(4-methylthiazol-5-yl)methyl]-3H-indazol-3-one (Ex. 111) as a solid (1.25 g), m.p. 145° C. (recrystallised from ethyl acetate), in 32% yield.

Using a similar procedure hydrolysis of the appropriate 1,2-dihydro-1-carboethoxy-2-substituted-3H-indazol-3-one of formula C (Ra=Rb=H; Rd=CO$_2$Et) gave the following compounds of formula B (Ra=Rb=H):

| Example | A | Q | m.p. (°C.) | reaction duration (hours) | yield (%) |
|---|---|---|---|---|---|
| 112[a] | —CH$_2$— | 2-pyridyl | 137–138 | 15 | 78 |
| 113 | —CH$_2$— | 2-methylpyrid-5-yl | 185–186 | 0.5 | 65 |
| 114 | —CH$_2$— | 3-methylpyrid-5-yl | 191–192 | 0.2 | 83 |
| 115 | —CH$_2$— | 2-methylpyrid-3-yl | 175–178 | 0.5 | 33 |
| 116 | —CH$_2$— | 2-chloropyrid-5-yl | 190 | 0.5 | 36 |
| 117 | —CH$_2$— | 2-chloropyrid-3-yl | 161–162 | 0.5 | 58 |
| 118 | —CH$_2$— | 3-bromopyrid-5-yl | 185–187 | 0.5 | 58 |
| 119 | —CH$_2$— | 2-methoxypyrid-5-yl | 176–177 | 0.5 | 46 |
| 120 | —CH$_2$— | 6-(4-chlorophenyl)-2-methylpyrid-3-yl | 222–225 | 0.5 | 26 |
| 121 | —CH$_2$— | 2,4-dimethylthiazol-5-yl | 202 | 0.5 | 32 |
| 122 | —CH$_2$— | pyrazinyl | 161–162 | 0.5 | 42 |
| 123 | —CH$_2$— | 5-thiazolyl | 191–192 | 0.5 | 26 |
| 124[b+] | —CH$_2$— | 2-benzofuranyl | 205–218 | 0.5 | 75 |
| 125[c] | —CH$_2$— | 2-quinolyl | 170–172 | 0.25 | 81 |
| 126[c+] | —CH$_2$— | 1-isoquinolyl | 150–155 | 0.25 | 72 |
| 127[b+] | —CH$_2$— | 8-quinolyl | 176–177 | 0.5 | 82 |
| 128 | —CH$_2$— | m-tolyl | 179 | 0.5 | 88 |
| 129 | —CH$_2$— | 3-fluorophenyl | 197 | 0.5 | 51 |
| 130 | —CH$_2$— | 3-bromophenyl | 192 | 0.5 | 57 |
| 131[d] | —CH$_2$— | 2-bromophenyl | 169–170 | 1 | 74 |
| 132 | —CH$_2$— | 3-nitrophenyl | 193 | 0.5 | 63 |
| 133[e+] | —CH$_2$— | 2-nitrophenyl | 166–170 | 0.5 | 27 |
| 134[f] | —CH$_2$— | 4-cyanophenyl | 180–182 | 1.5 | 59 |
| 135 | —CH$_2$— | 3-cyanophenyl | 179 | 0.5 | 74 |
| 136 | —CH$_2$— | 3-trifluoromethylphenyl | 176–177 | 0.5 | 76 |
| 137 | —CH$_2$— | 4-biphenylyl | 196–198 | 2 | 88 |
| 138 | —CH$_2$— | 3-biphenylyl | 170 | 0.25 | 88 |
| 139[g] | —CH$_2$— | benzyloxy | 116–118 | 0.33 | 80 |
| 140 | direct link | cyclohex-2-en-1-yl | 120–123 | 0.25 | 63 |
| 141[c] | direct link | 2-methylprop-2-en-1-yl | 108–110 | 0.25 | 63 |
| 142[h] | —CH$_2$— | cyano | 168–170 | 0.5 | 32 |

NOTES

[+]The starting material was a mixture of the N-alkylated-3H-indazol-3-one and the corresponding O-alkylated-1H-indazole, the preparation of which is described in the portion of Examples 143–148 which concerns the preparation of starting materials.
[a]The product was purified by column chromatography using methylene chloride/diethyl ether/methanol (5/5/0.2 v/v) as eluant. The resultant solid was recrystallised from a mixture of diethyl ether and methanol.
[b]The hydrolysis was done at ambient temperature.
[c]The reaction mixture was acidified to pH 7.
[d]The product was purified by column chromatography using methylene chloride/diethyl ether (9/1 v/v) as eluant and then recrystallised from diethyl ether.
[e]The hydrolysis was done at ambient temperature. The basic reaction mixture was partitioned between diethyl ether and water. The aqueous layer was acidified to pH 5 with acetic acid and the product was extracted into methylene chloride.
[f]The hydrolysis was done at 60° C.
[g]One equivalent of powdered potassium hydroxide was used. The product was purified by column chromatography using methylene chloride/diethyl ether (4/1 v/v) as eluant and then recrystallised from a mixture of diethyl ether and pentane.
[h]The product was purified by column chromatography using methylene chloride/diethyl ether (4/1 v/v) as eluant and then recrystallised from ethyl acetate.

EXAMPLES 143–148

A mixture (1.6 g) of 1,2-dihydro-1-carboethoxy-2-(3-phenylprop-2ynyl)-3H-indazol-3-one and 1-carboethoxy-3-[(3-phenylprop-2-ynyl)oxy]-1H-indazole obtained as described below was dissolved in methanol (5 ml) and 2M sodium hydroxide (5 ml) was added. The mixture was stirred and heated to 50° C. for 1 hour. The methanol was evaporated and the residue was diluted with water (15 ml). The solution was neutralised with M hydrochloric acid and extracted with ethyl acetate (x3). The combined extracts were washed with a saturated aqueous sodium chloride solution, dried (MgSO₄) and evaporated. The residue crystallised on trituration under diethyl ether and the solid (0.74 g) was purified by column chromatography eluting with methylene chloride/methanol (19/1 v/v). The product was recrystallised from diethyl ether to give 1,2-dihydro-2-(3-phenylprop-2-ynyl)-3H-indazol-3-one (Ex. 143) (0.47 g), m.p. 151–154° C.

Using a similar hydrolysis procedure but employing the appropriate mixture of N- and O-alkylated compounds of formulae C and D respectively (Ra=Rb=H; Rd=CO$_2$Et) the following compounds of formula B (Ra=Rb=H) were obtained:

| Example | A | Q | m.p. (°C.) | reaction duration (hours) | Yield (%) |
|---|---|---|---|---|---|
| 144 | direct link | trans-cinnamyl | 164–165 | 2 | 44 |
| 145 | —CH$_2$— | 1-methylimidazol-2-yl | 147–151 | 0.75 | 14 |
| 146 | —CH$_2$— | 1-benzylimidazol-2-yl | 182–186 | 1 | 28 |
| 147* | —CH$_2$— | 6-methoxypyridazin-3-yl | 156–158 | 1 | 9 |
| 148** | —CH$_2$— | 6-chloropyridazin-3-yl | 176 | 1.5 | 29 |

Notes
*In the mixture of starting materials Q was 6-chloropyridazin-3-yl. The hydrolysis was carried out at ambient temperature rather than at 50° C.
**Lithium hydroxide was used in place of sodium hydroxide, dimethoxyethane was used in place of methanol and the reaction was carried out at ambient temperature rather than at 50° C.

The necessary starting mixtures of N- and O-alkylated compounds of formulae C (Ra=Rb=H; Rd=CO$_2$Et)

and D (Ra=Rb=H; Rd=CO₂Et) were obtained as follows:

1,2-Dihydro-1-carboethoxy-3H-indazol-3-one (1.03 g) was added portionwise to a stirred suspension of sodium hydride (240 mg of a 50% dispersion in oil from which the oil was removed by washing the dispersion with petrol (60–80° C.) under an atmosphere of argon) in N,N-dimethylformamide (5 ml) which was cooled to 0° C. and maintained under an atmosphere of argon. After 30 minutes trans-cinnamyl bromide (1.08 g) was added dropwise and the mixture was stirred at ambient temperature for 4 hours. The reaction mixture was diluted with water (20 ml), acidified to pH2 with M hydrochloric acid and extracted with ethyl acetate. The extracts were washed with a saturated aqueous sodium chloride solution, dried (MgSO₄) and evaporated to leave as an oil (1.2 g, 75%), a mixture of 1,2-dihydro-1-carboethoxy-2-trans-cinnamyl-3H-indazol-3-one and 1-carboethoxy-3-trans-cinnamyloxy-1H-indazole (starting material for Ex. 144).

Using a similar alkylation procedure but employing the appropriate alkyl bromide the following mixtures of compounds of formula C (Ra=Rb=H; Rd=CO₂Et)) and of formula D (Ra=Rb=H; Rd=CO₂Et) were obtained:

| Starting material for Example | A | Q | reaction duration (hours) | Yield (%) |
|---|---|---|---|---|
| 143 | —CH₂— | 2-phenylethynyl | 1 | 100 |
| 148* | —CH₂— | 6-chloropyridazin-3-yl | 3.5 | 44 |

Notes
*3-Chloro-6-chloromethylpyridazine (prepared by the reaction of N-chlorosuccinimide and 3-chloro-6-methylpyridazine which is itself described in the Journal of the Chemical Society, 1947, 239) was used rather than an alkyl bromide.

2-Chloromethyl-1-methylimidazole (0.91 g) was added portionwise to a stirred mixture of 1,2-dihydro-1-carboethoxy-3H-indazol-3-one (1.03 g), caesium carbonate (5.4 g) and N,N-dimethylformamide (DMF, 5 ml). The mixture was heated to 80° C. for 4 hours under an atmosphere of argon, cooled to ambient temperature and filtered. The filtrate was diluted with water and extracted with ethyl acetate. The solid was washed with ethyl acetate. The organic solutions were combined, washed with a saturated aqueous sodium chloride solution, dried (MgSO₄) and evaporated. The oil residue crystallised on trituration under diethyl ether. There was thus obtained a mixture (1 g, 67% of 1,2-dihydro-1-carboethoxy-2-(1-methylimidazol-2-yl)methyl-3H-indazol-3-one and 1-carboethoxy-3-(1-methylimidazol-2-yl)methoxy-1H-indazole (starting material for Ex. 145).

Using a similar alkylation procedure but employing the appropriate alkyl chloride the following mixtures of compounds of formula C (Ra=Rb=H; Rd=CO₂Et) and of formula D (Ra=Rb=H; Rd=CO₂Et) were obtained:

| Starting material for Example | A | Q | Physical Form | reaction duration (hours) | yield (%) |
|---|---|---|---|---|---|
| 146 | —CH₂— | 1-benzylimidazol-2-yl | oil | 1 | 74 |
| 124 | —CH₂— | 2-benzofuranyl | oil | 1.5 | 30 |
| 126ᵃ | —CH₂— | 1-isoquinolyl | oil | 3 | 25 |
| 127ᵇ | —CH₂— | 8-quinolyl | oil | 2 | 38 |

ᵃThe alkyl bromide (Journal of the Chemical Society, 1951, 1145) was used in place of the alkyl chloride, potassium carbonate was used in place of caesium carbonate and the reaction was carried out at ambient temperature. After chromatography the compound of formul C (Ra=Rb=H, Rd=CO₂Et) could be obtained as a solid, m.p. 156–159° C.
ᵇThe alkyl bromide (Helvetica Chimica Acta, 1954, 3790) was used in place of the alkyl chloride, potassium carbonate was used in place of caesium carbonate and the reaction was carried out at ambient temperature. After chromatography the compound of formula C(Ra=Rb=H, Rd=CO₂Et) could be obtained as a solid, m.p. 122–124° C.

Using a similar alkylation procedure to that employed in Example 35, but using 2-nitrobenzyl bromide instead of bromodiphenylmethane, having a reaction duration of 48 hours and omitting the column chromatography there was obtained a mixture in 79% yield of 1,2-dihydro-1-carboethoxy-2-(2-nitrobenzyl)-3H-indazol-3-one and 1-carboethoxy-3-(2-nitrobenzyloxy)-1H-indazole (starting material for Ex. 133).

EXAMPLE 149

Using a similar procedure to that described in Examples 52–53, but starting from 1,2-dihydro-2-phenylthiomethyl-3H-indazol-3-one (Example 38), there was obtained 1,2-dihydro-2-phenylsulphinylmethyl-3H-indazol-3-one as a solid, m.p. 149–150° C. (recrystallised from diethyl ether) in 42% yield.

EXAMPLE 150

A mixture of 1,2-dihydro-2-(3-phenylprop-2ynyl)-3H-indazol-3-one (364 mg, Ex. 143), quinoline (5 drops), palladium-on-barium sulphate catalyst (36 mg) and methanol (15 ml) was stirred at ambient temperature under an atmosphere of hydrogen for 5 minutes. The mixture was filtered and the filtrate was evaporated. The residue was purified by column chromatography eluting with methylene chloride/ether/methanol (80/17/3 v/v) to give 1,2-dihydro-2-cis-cinnamyl-3H-indazol-3-one as a solid (240 mg), m.p. 116–121° C. (recrystallised from ethyl acetate) in 65% yield.

EXAMPLES 151–152

1,2-Dihydro-2-(2-aminobenzyl)-3H-indazol-3-one (Ex. 151) was obtained as a solid of m.p. 204–205° C., in 70% yield, using a similar procedure to that described in Examples 2–16 starting from N-(2-aminobenzyl)-2-nitrobenzamide except that the reaction duration was 16 hours, a mixture of ethanol and water (95/5 v/v) was used in place of aqueous methanol as the reaction solvent, in the work-up the reaction mixture was acidified to pH1 with hydrochloric acid and washed with methylene chloride, the acidity was reduced to pH5 with M sodium hydroxide solution and the mixture was extracted with methylene chloride.

N-(2-Aminobenzyl)-2-nitrobenzamide was itself obtained as a solid, m.p. 112–113° C., in 80% yield using a similar procedure to that described for the starting material of Example 24, that is by reacting 2-nitrobenzoyl chloride with 2-aminobenzyl (J.Amer.Chem.Soc., 1949, 71, 2137) except that, after the work-up described therein was complete, the residue was triturated in a mixture of diethyl ether/methylene chloride/methanol (1/1/ few drops v/v). The crystalline solid, formed by reaction of the acid chloride with both of the amino groups of 2-aminobenzylamine, was filtered off and discarded. The residual solution was concentrated and N-(2-aminobenzyl)-2-nitrobenzamide was precipitated by the addition of diethyl ether.

Acetyl chloride (314 mg) was added dropwise to a stirred mixture of the indazolone prepared above (Ex. 151, 478 mg), triethylamine (404 mg) and methylene chloride (25 ml) and the mixture was stirred at ambient temperature for 5 minutes. The solvent was evaporated and the residue was purified by column chromatography using methylene chloride/diethyl ether/methanol (60/40/1 v/v) as eluant to give, as the second component of a three component reaction mixture, 1,2-dihydro-2-(2-diacetylaminobenzyl)-3H-indazol-3-one (Ex. 152) as a solid (400 mg), m.p. 114–115° C. (recrystallised from diethyl ether) in 62% yield.

EXAMPLE 153

A mixture of 1,2-dihydro-2-(3-nitrobenzyl)-3H-indazol-3-one (0.5 g, Ex 132), platinum oxide catalyst (50 mg) and tetrahydrofuran (100 ml) was stirred under an atmosphere of hydrogen for 2 hours. The mixture was filtered through celite and the filtrate was evaporated to give 1,2-dihydro-2-(3-aminobenzyl)-3H-indazol-3-one as a solid (21 mg), m.p. 143–145° C. (recrystallised three times from ethyl acetate), in 5% yield after the recrystallisations.

EXAMPLE 154

A mixture of 1,2-dihydro-3-acetamidobenzyl-1-t-butoxycarbonyl-3H-indazol-3-one (0.5 g) and trifluoroacetic acid (10 ml) was stirred at 0° C. for 1 hour and then evaporated to dryness. There was thus obtained 1,2-dihydro-3-acetamidobenzyl-3H-indazol-3-one as a solid, m.p. 255° C., in 40% yield.

The starting material was obtained as follows: A mixture of 1,2-dihydro-3H-indazol-3-one (2.7 g), pyridine (3.1 ml) and methylene chloride (15 ml) was stirred at ambient temperature for 15 minutes, di-t-butyl dicarbonate (6.2 g) was added and the mixture was stirred at ambient temperature for 16 hours. The organic solution was acidified to pH5 with dilute aqueous hydrochloric acid, washed with water and evaporated. The residue was triturated in ethyl acetate to give 1,2-dihydro-1-t-butoxycarbonyl-3H-indazol-3-one as a white solid, m.p. 145° C., in 23% yield.

This product was alkylated using a similar alkylation procedure to that described in Example 35 but using 3-nitrobenzyl bromide in place of bromodiphenylmethane. There was thus obtained 1,2-dihydro-1-t-butoxycarbonyl-2-(3-nitrobenzyl)-3H-indazol-3-one as an oil of satisfactory purity in 75% yield.

A mixture of this product (4.05 g), platinum oxide catalyst (0.4 g) and tetrahydrofuran (100 ml) was stirred under an atmosphere of hydrogen for 11 hours. A second portion of catalyst (0.2 g) was added and the reaction was continued for 2 hours. The mixture was filtered through celite and the filtrate was evaporated. The residue was purified by column chromatography to give 1,2-dihydro-2-(3-aminobenzyl)-1-t-butoxycarbonyl-3H-indazol-3-one as a solid, m.p. 155° C., in 45% yield.

Acetyl chloride (0.5 g) was added dropwise to a stirred mixture of the 3-aminobenzyl produce (0.4 g), triethylamine (0.33 ml) and methylene chloride (25 ml) which had been cooled to 0° C. After 1 hour further portions of triethylamine (0.2 ml) and acetyl chloride (0.38 g) were added and the mixture was stirred at ambient temperature for 16 hours. The mixture was washed with water, dried (MgSO4) and evaporated. The residue was purified by column chromatography to give 1,2-dihydro-2-(3-acetamidobenzyl)-1-t-butoxycarbonyl-3H-indazol-3-one as an oil of satisfactory purity in 95% yield.

EXAMPLE 155

The procedure described in Example 1 was repeated using 4-fluoro-2-nitro-N-(3-pyridylmethyl)benzamide (obtained as a solid, m.p. 148–149°0 C., by reaction of 4-fluoro-2-nitrobenzoic acid and thionyl chloride, followed by the reaction of the benzoyl chloride so formed and 3-(aminomethyl)pyridine using the process described for the preparation of the starting material for Ex. 24) as starting material but with a reaction duration of 5 hours and using ethanol/water (4/1 v/v) as solvent. There was thus obtained 1,2-dihydro-6-fluoro-2-(3-pyridylmethyl)-3H-indazol-3-one (Ex. 155) as a solid, m.p. 205–210° C. (recrystallised from methylene chloride), in 50% yield.

EXAMPLES 156–159

Using a similar procedure to that described in Examples 2–16, but starting from the appropriate N-substituted-2-nitrobenzamide of formula A (Ra=Rb=H), the following compounds of formula B (Ra=Rb=H) were obtained:

| Example | A | Q | m.p.* (°C.) | reaction duration (hours) | yield % |
|---|---|---|---|---|---|
| 156 | —CH2— | 2,3-dimethylphenyl | 195–197 | 4 | 58 |
| 157 | —CH2— | 2,3-methylenedioxyphenyl | 173–175 | 4 | 35 |
| 158[a] | —CH2— | 3-hydroxymethylphenyl | 180 | 4 | 25 |
| 159 | —CH(Et)— | 3-pyridyl | 128–129 | 3 | 24 |

Notes
*Reaction time with zinc dust and sodium hydroxide but using a mixture of ethanol and water (95/5 v/v) in place of aqueous methanol as the reaction solvent.
[a]The reaction solvent was a mixture of ethanol and water (7/3 v/v).

The necessary starting 2-nitrobenzamide derivatives of formula A (Ra=Rb=H) were obtained using similar procedures to those described for the starting materials for Examples 1 and 24, that is by reacting ethyl 2-nitrobenzoyl carbonate or 2-nitrobenzoyl chloride with the appropriate amine of the formula H2N—A—Q, and had the following characteristic properties:

| Starting material for Ex. No. | A | Q | m.p. (°C.) |
|---|---|---|---|
| 156 | —CH2— | 2,3-dimethylphenyl | 155–156 |
| 157[a] | —CH2— | 2,3-methylenedioxyphenyl | 148–149 |
| 158[b] | —CH2— | 3-hydroxymethylphenyl | 122 |

-continued

| Starting material for Ex. No. | A | Q | m.p. (°C.) |
|---|---|---|---|
| 159[c] | —CH(Et)— | 3-pyridyl | ** |

Notes
**Where no melting point is given the compound was obtained as a solid of satisfactory purity as judged by TLC, IR and/or NMR analysis.
[a]2,3-Methylenedioxybenzylamine was prepared from 2,3-methylenedioxybenzaldehyde (Can. J. Chem., 1970, 48, 948) as follows:-A solution of hydroxylamine hydrochloride (0.67 g) in water (1 ml) was added to a solution of the aldehyde (1.1 g) in hot ethanol (3 ml). A solution of sodium hydroxide (0.45 g) in water (1 ml) was then added and the mixture was stirred at ambient temperature for 20 hours. Ice (10 g) and solid carbon dioxide (2 g) were added and the mixture was stirred till it warmed to ambient temperature. The product 2,3-methylenedioxybenzaldehyde oxime (1.1 g) was filtered off, m.p. 133–134° C. in 83% yield. A solution of the oxime (1 g) in acetic acid (6 ml) was heated to 60° C. and zinc (1.56 g) was added portionwise over 45 minutes. The mixture was heated to 60° C. for a further 45 minutes. The mixture was cooled, filtered and the filtrate was evaporated to give 2,3-methylenedioxybenzylamine as an oil (0.75 g) in 81% yield.
[b]The amine starting material was obtained by reduction of a solution of 3-cyanobenzaldehyde in diethyl ether with lithium aluminum hydride. The amidification reaction was carried out at ambient temperature.
[c]3-(1-Aminopropyl)pyridine was prepared as described in Acta Chem. Scand., 1963, 17, 1717.

EXAMPLES 160–172

Using a similar procedure to that described in Examples 2–16, but starting from the appropriate N-substituted-2-nitrobenzamide of formula A (A=CH$_2$, Q=3-pyridyl), the following compounds of formula B (A=CH$_2$, Q=3-pyridyl) were obtained:

| Example | Ra | Rb | m.p. (°C.) | reaction duration (hours) | yield % |
|---|---|---|---|---|---|
| 160 | 4-methyl | H | 158–160 | 4* | 15 |
| 161 | 5-methyl | H | 150–151 | 6*** | 10 |
| 162 | 6-methyl | H | 197 | 5* | 10 |
| 163 | 4-methoxy | H | 170 | 2.5*** | 26 |
| 164 | 5-methoxy | H | 134 | 4** | 21 |
| 165 | 6-methoxy | H | 173 | 5** | 25 |
| 166 | 5-methoxy | 6-methoxy | 142–145 | 5** | 20 |
| 167 | 4-ethoxy | H | 160 | 5** | 8 |
| 168 | 5-ethoxy | H | 144 | 6** | 30 |
| 169 | 5-isopropoxy | H | 104 | 3** | 47 |
| 170 | 5-chloro | H | 214–216 | 1.5* | 31 |
| 171 | 6-chloro | H | 224–225 | 4* | 78 |
| 172 | 4-fluoro | H | 179–183 | 5* | 43 |

Notes
*Reaction time with zinc dust and sodium hydroxide but using a mixture of ethanol and water (3/2 v/v) in place of aqueous methanol as the reaction solvent.
**The reaction solvent was a mixture of ethanol and water (7/3 v/v).
***The reaction solvent was a mixture of ethanol and water (95/5 v/v).

The necessary starting 2-nitrobenzamide derivatives of formula A (A=CH$_2$, Q=3-pyridyl) were obtained using similar procedures to those described for the starting materials for Examples 1 and 24, that is by reacting ethyl 2-nitrobenzoyl carbonate or 2-nitrobenzoyl chloride with the appropriate amine of the formula H$_2$N—A—Q, except that the reaction was carried out at ambient temperature. The benzamides had the following characteristic properties:

| Starting material for Ex. No. | Ra | Rb | m.p. (°C.) |
|---|---|---|---|
| 160 | 6-methyl | H | 138–139 |
| 161 | 5-methyl | H | 130–132 |
| 162 | 4-methyl | H | + |
| 163[a] | 6-methoxy | H | + |
| 164[b] | 5-methoxy | H | 137 |
| 165[c] | 4-methoxy | H | 173 |
| 166 | 4-methoxy | 5-methoxy | 132–134 |
| 167[a] | 6-ethoxy | H | + |
| 168[b] | 5-ethoxy | H | + |
| 169[b] | 5-isopropoxy | H | + |
| 170 | 5-chloro | H | + |
| 171 | 4-chloro | H | + |
| 172[d] | 6-fluoro | H | 108–110 |

Notes
+ Where no melting point is given the compound was obtained as a solid of satisfactory purity as judged by TLC, IR and/or NMR analysis.
[a]The appropriate 6-alkoxy-2-nitrobenzoic acid was prepared from 6-hydroxy-2-nitrobenzoic acid using the method described in footnote e. of the portion of Examples 58–72 which is concerned with the preparation of starting materials, except that the appropriate alkyl iodide was used in place of butyl iodide.
[b]The appropriate 5-alkoxy-2-nitrobenzoic acid was prepared from 5-hydroxy-2-nitrobenzoic acid using the method mentioned in footnote [a] immediately above.
[c]4-Methoxy-2-nitrobenzoic acid was prepared from 4-hydroxy-2-nitrobenzoic acid using the method described in the portion of Example 82 which is concerned with the preparation of starting materials, except that methyl iodide was used in place of butyl iodide.
[d]6-Fluoro-2-nitrobenzoic acid is described in Chem. Ber., 1896, 29, 841.

EXAMPLES 173–176

Using a similar procedure to that described in Examples 2–16, but starting from the appropriate N-substituted-2-nitrobenzamide of formula A (A=CH$_2$, Q=phenyl), the following compounds of formula B (A=CH$_2$, Q=phenyl) were obtained:

| Example | Ra | Rb | m.p. (°C.) | reaction duration (hours) | Yield % |
|---|---|---|---|---|---|
| 173 | 6-methyl | H | 209 | 7*** | 57 |
| 174 | 6-methoxy | H | 173 | 1.3** | 73 |
| 175[a] | 5-methoxy | 6-methoxy | 190–193 | 5* | 8 |
| 176[a] | 5-ethoxy | 6-methoxy | 161–164 | 5* | 12 |

Notes
*The reaction solvent was a mixture of ethanol and water (3/2 v/v).
**The reaction solvent was a mixture of ethanol and water (4/4 v/v).
***The reaction solvent was a mixture of ethanol and water (95/5 v/v).
[a]Cyclisation of N-benzyl-4,5-dimethoxy-2-nitrobenzamide gave a mixture of two products which were separated by chromatography using methylene chloride/diethyl ether/methanol (50/50/1 v/v) as eluant. There were thus obtained 1,2-dihydro-2-benzyl-4,5-dimethoxy-3H-indazol-3-one and 1,2-dihydro-2-benzyl-4-ethoxy-5-methoxy-3H-indazol-3-one.

The necessary starting 2-nitrobenzamide derivatives of formula A (A=CH$_2$, Q=phenyl) were obtained using similar procedures to those described for the starting materials for Examples 1 and 24, that is by reacting ethyl 2-nitrobenzoyl carbonate or 2-nitrobenzoyl chloride with the appropriate amine of the formula H$_2$N—A—Q, except that the reaction was carried out at ambient temperature. The benzamides had the following characteristic properties:

| Starting Material for Ex. No. | Ra | Rb | m.p. (°C.) |
|---|---|---|---|
| 173 | 4-methyl | H | + |
| 174 | 4-methoxy | H | + |
| 175 | 4-methoxy | 5-methoxy | 132–134 |

Notes
+ Where no melting point is given the compound was obtained as a solid of satisfactory purity as judged by TLC, IR and/or NMR analysis.

EXAMPLES 177-178

Using a similar procedure to that described in Examples 2-16, but starting from 2-nitro-N-(prop-2-ynyl)benzamide (itself prepared from 2-nitrobenzoyl chloride and prop-2-ynylamine using the process described for the preparation of the starting material for Ex. 24), using a mixture of ethanol and water (95/5 v/v) in place of aqueous methanol as the reaction solvent and having a reaction duration of 3 hours, there was obtained 1,2-dihydro-2-allenyl-3H-indazol-3-one (Ex. 177) as a solid, m.p. 126-130° C. in 12% yield.

Using a similar procedure to that described in Examples 2-16, but starting from N-allyl-4-methoxy-2-nitrobenzamide (itself prepared from 4-hydroxy-2-nitrobenzoic acid using the procedure described in the portion of Example 82 which is concerned with the preparation of starting material except that methyl iodide was used in place of butyl iodide and allylamine was used in place of benzylamine), using a mixture of ethanol and water (4/1 v/v) in place of aqueous methanol as the reaction solvent and having a reaction duration of 3 hours, there was obtained 1,2-dihydro-2-allyl-6-methoxy-3H-indazol-3-one (Ex. 178) as a solid, m.p. 126° C. in 33% yield.

EXAMPLE 179

The procedure described in Example 31 was repeated using N-[2-(1-methylpyrrol-2-yl)ethyl]-2-nitrobenzamide (obtained as a solid, m.p. 103° C., from 2-nitrobenzoyl chloride and 2-(1-methylpyrrol-2-yl)ethylamine and carrying out the reaction under reflux for 5 hours. There was thus obtained 1,2-dihydro-2-[2-(1-methylpyrrol-2-yl)ethyl]-3H-indazol-3-one (Ex. 179) as a solid, m.p. 125-133° C. in 58% yield.

EXAMPLES 180-184

Using a similar alkylation procedure to that described in Example 35, but using the appropriate alkyl bromide instead of bromodiphenylmethane, there were obtained the following compounds of formula C (Ra=Rb=H; Rd=CO$_2$Et):

| Example | A | Q | m.p.* (°C.) | reaction duration (hours) | yield % |
|---|---|---|---|---|---|
| 180[a] | —CH$_2$— | 1,2-dihydro-1-carboethoxy-3-oxo-3H-indazol-2-yl | 169-170 | 5 | 52 |
| 181 | —CH$_2$— | 2-biphenylyl | oil | 24 | 21 |
| 182[b] | —CH$_2$— | 2-pyridylthio | oil | 6 | 15 |
| 183[c] | —CH$_2$— | phenoxy | oil | 0.2 | 61 |
| 184[d] | —(CH$_2$)$_2$— | 4-pyridyl | oil | 0.5 | 40 |

Notes
*Where the product was obtained as an oil it was shown to be of satisfactory purity as judged by TLC, IR and/or NMR analysis.
[a]1,2-Dihydro-1-carboethoxy-2-(1,2-dihydro-1-carboethoxy-3-oxo-3H-indazol-2-ylmethyl)-3H-indazol-3-one was prepared as follows:-A mixture of 1,2-dihydro-1-carboethoxy-3H-indazol-3-one (3.1 g), triethylamine (3 g), chloroiodomethane (5.3 g) and chloroform (75 ml) was heated to reflux for 4 hours. The mixture was cooled and filtered and the filtrate was evaporated. The residue was chromatograph using a mixture of methylene chloride and ether (9:1 v/v) as eluant to give the product (Ex. 180) as a solid (0.58 g).
[b]2-Chloromethylthiopyridine was obtained as described in Synthesis, 1986, 835.
[c]Chloromethyl phenyl ether was prepared as described in Chem. Ber., 1963, 96, 2275.
[d]4-(2-Bromoethyl)pyridine, as a hydrobromide salt of satisfoactory purity, was obtained by heating to reflux a mixture of 2-(pyrid-4-yl)ethanol (itself prepared by the reduction of ethyl 4-pyridylacetate with lithium aluminium hydride) and hydrobromic acid (48%).

EXAMPLES 185-194

Using a similar alkylation procedure to that described in Example 39, but using the appropriate alkyl bromide rather than 4-nitrobenzyl bromide, there were obtained the following compounds of formula C (Ra=Rb=H; Rd=CO$_2$Et):

| Example | A | Q | m.p.* (°C.) | reaction duration (hours) | yield % |
|---|---|---|---|---|---|
| 185[a] | —CH$_2$— | 2-methylthiazol-5-yl | oil | 1 | 11 |
| 186[b] | —CH$_2$— | 4-thiazolyl | oil | 1.3 | 6 |
| 187[c] | —CH$_2$— | 5-isoxazolyl | 75 | 0.8 | 22 |
| 188[d] | —CH$_2$— | 3,5-dimethylisoxazol-4-yl | 110 | 2.5 | 20 |
| 189[e] | —CH$_2$— | 4-methylpyrid-3-yl | oil | 0.5 | 15 |
| 190[f] | —CH$_2$— | 3-chloropyrid-5-yl | 104 | 0.5 | 27 |
| 191[g] | —CH$_2$— | 3-fluoropyrid-5-yl | oil | 0.5 | 24 |
| 192[h] | —CH$_2$— | 2-methoxypyrid-4-yl | oil | 0.5 | 17 |
| 193[i] | —CH$_2$— | 2-bromopyrid-4-yl | oil | 0.5 | 24 |
| 194[j] | —CH$_2$— | 3-bromopyrid-4-yl | oil | 0.5 | 10 |

Notes
*Where the product was obtained as an oil, it was shown to be of satisfactory purity as judged by TLC, IR and/or NMR analysis.
[a]5-Chloromethyl-2-methylthiazole, used in place of the corresponding bromide, is described in J. Amer. Chem. Soc., 1982, 104, 4461.
[b]4-Chloromethylthiazole, used in place of the corresponding bromide, is described in J. Amer. Chem. Soc., 1951, 73, 2935.
[c]5-Bromomethylisoxazole was prepared by heating to reflux a mixture of 5-methylisoxazole and N-bromosuccinimide in carbon tetrachloride using irradiation from a 250 Watt lamp to initiate the reaction.
[d]4-Chloromethyl-3,5-dimethylisoxazole was used in place of the corresponding bromide.
[e]3-Bromomethyl-4-methylpyridine was prepared by the reaction of 3,4-lutidine and N-bromosuccinimide using the procedure described in note [c] above.
[f]3-Bromomethyl-5-chloropyridine was prepared by the reaction of 3-chloro-5-methylpyridine (itself prepared from 3-amino-5-methylpyridine by the process described in Chem. Abs., 95, 115214b, that is diazotisation and reaction of the diazonium salt with cuprous chloride) and N-bromosuccinimide using the procedure described in note [c] above.
[g]3-Bromomethyl-5-fluropyridine was prepared by the reaction of 3-fluoro-5-methyl-pyridine (J. Org. Chem., 1949, 14, 328) and N-bromosuccinimide using the procedure described in note [c] above.
[h]4-Bromomethyl-2-methoxypyridine was prepared by the reaction of 2-methoxy-4-methylpyridine (J. Amer. Chem. Soc., 1957, 79, 3164) and N-bromosuccinimide using the procedure described in note [c] above.
[i]2-Bromo-4-bromomethylpyridine was prepared by the reaction of 2-bromo-4-methylpyridine (J. Amer. Chem. Soc., 1949, 71, 72) and N-bromosuccinimide using the procedure described in note [c] above.
[j]3-Bromo-4-bromomethylpyridine was prepared by the reaction of 3-bromo-4-methylpyridine (Bull. Soc. Chim, Fr., 1976, 530) and N-bromosuccinimide using the procedure described in note [c] above.

EXAMPLES 195-197

Using a similar alkylation procedure to that described in Example 108, but using the appropriate alkyl chloride in place of 2-chloromethylquinoline hydrochloride, there were obtained the following compounds of formula C (Ra=Rb=H; Rd=CO$_2$Et):

| Example | A | Q | m.p.* (°C.) | reaction duration (hours) | yield % |
|---|---|---|---|---|---|
| 195[a] | —CH$_2$— | 3-quinolyl | oil | 5 | 61 |
| 196[b] | —CH$_2$— | 4-isoquinolyl | 148-151 | 8 | 24 |
| 197[c] | —CH$_2$— | 3-pyridyl | oil | 13 | 15 |

Notes
*Where the product was obtained as an oil it was shown to be of satisfactory purity as judged by TLC, IR and/or NMR analysis.
[a]3-Bromomethylquinoline is described in J. Chem. Soc., 1951, 1145.
[b]4-Chloromethylisoquinoline is described in J. Org. Chem., 1980, 45, 1557.
[c]Ex. 197, Ra = 7-methyl, Rb = H; 1,2-Dihydro-1-carboethoxy-7-methyl-3H-indazol-3-one used as starting material was prepared as follows:-1,2-Dihydro-7-methyl-3H-indazol-3-one was prepared from 2-amino-3-methylbenzoic acid, in 67% yield, using the method described in J. Med. Chem., 1984, 27, 768, except that stannous chloride was used instead of sodium sulphite to reduce the intermediate diazonium salt. The product so obtained was treated with ethyl chloroformate using the method described in the reference given immediately above to give in 8% yield 1,2-dihydro-1-carboethoxy-7-methyl-3H-indazol-3-one.

EXAMPLES 198-212

Using a similar alkylation procedure to that described in Example 109, that is using the appropriate alkyl bromide as the alkylating agent, using potassium carbonate as the base, using N,N-dimethylformamide as the solvent and carrying out the reaction at ambient temperature there were obtained the following compounds of formula C (Ra=Rb=H; Rd=$CO_2Et$):

| Example | A | Q | m.p.* (°C.) | reaction duration (hours) | yield % |
|---|---|---|---|---|---|
| 198[a] | —$CH_2$— | 4-quinolyl | oil | 17 | 42 |
| 199[b] | —$CH_2$— | 2-aminothiazol-4-yl | 215-217 | 64 | 12 |
| 200[c] | —$CH_2$— | 3-pyrazolyl | 152-155 | 2 | 35 |
| 201[c] | —$CH_2$— | 4-pyrazolyl | 158-160 | 2 | 41 |
| 202[d] | —$CH_2$— | 1,2,3-triazol-4-yl | 148-150 | 2 | 38 |
| 203[e] | —$CH_2$— | 1,2,5-thiadiazol-3-yl | oil | 3 | 26 |
| 204[f] | —$CH_2$— | 1,2,3-thiadiazol-4-yl | oil | 2 | 28 |
| 205[g] | —$CH_2$— | 1-t-butoxy-carbonyl-indol-3-yl | 106-108 | 12 | 37 |
| 206[h] | —$(CH_2)_2$— | 3-pyridyl | oil | 16 | 10 |
| 207 | direct link | 2-propynyl | oil | 2 | 55 |
| 208[i] | direct link | methylallyl | oil | 13 | 8 |
| 209[j] | —$CH_2$— | 1-methylimidazol-5-yl | oil | 2 | 21 |
| 210[k] | —$CH_2$— | 1-methylpyrazol-4-yl | oil | 16 | 20 |
| 211[l] | —$CH_2$— | 1,2,3-thiadiazol-5-yl | oil | 3 | 28 |
| 212[m] | —$CH_2$— | 5-isothiazolyl | oil | 16 | 20 |

Notes
*Where the product was obtained as an oil it was shown to be of satisfactory purity as judged by TLC, IR and/or NMR analysis.
[a]4-Bromomethylquinoline is described in J. Chem. Soc., 1951, 1145.
[b]The alkyl chloride (J. Amer. Chem. Soc., 1946, 68, 2155; purified by recrystallisation of its hydrochloride salt from isopropanol) was used in place of the alkyl bromide.
[c]The alkyl chloride (J. Amer. Chem. Soc., 1949, 71, 3994; purified by recrystallisation of its hydrochloride salt from ethyl acetate) was used in place of the alkyl bromide.
[d]4-Chloromethyl-1,2,3-triazole, as its hydrochloride salt, was prepared as an oilof satisfactory purity from methyl 1,2,3-triazole-4-carboxylate (Chem. Ber., 1970, 103, 1916) using the method described in Chem.Abs., 1969, 71, 38813w, of reduction with lithium aluminium hydride and chlorination iwth thionyl chloride. The product (Ex. 202) was purified by column chromatography eluting with a mixture of toluene and ethyl acetate (3/2 v/v).
[e]The alkyl bromide (purified by column chromatography eluting with toluene and ethyl acetate (4/1 v/v)) is described in J. Het. Chem., 1984, 21, 1157.
[f]The alkyl mesylate, used in place of the corresponding alkyl bromide, was prepared as an oil of satisfactory purity, by the reaction of a mixture of 4-hydroxymethyl-1,2,3-thiadiazole (Acta Pharm. Suec., 1973, 10, 285), mesyl chloride and triethylamine in methylene chloride at 5° C. The product (Ex. 204) was purified by column chromatography eluting with a mixture of toluene and ethyl acetate (3/1 v/v).
[g]3-Bromomethyl-1-t-butoxycarbonylindole, used as starting material was obtained, as an oil of satisfactory purity, from indole-3-carboxaldehyde using the processes described in Liebig's Ann. Chem., 1985, 413, that is t-butoxycarbonylation with di-t-butyl dicarbonate, reduction with sodium borohydride and bromination with bromine in the presence of triphenylphosphine.
[h]3-(2-Bromoethyl)pyridine is described in J. Het. Chem., 1973, 10, 39.
[i]Ex. 208, Ra=5-nitro, Rb=H; methylallyl chloride was used in place of the corresponding bromide and the reaction was carried out at a temperature of 40° C.
[j]The alkyl chloride, as its hydrochloride salt, is described in J. Amer. Chem. Soc., 1949, 71, 2444 and this was used in place of the corresponding alkyl bromide. The reaction mixture was stirred at ambient temperature for 2 hours and then heated to 60° C. for 18 minutes.
[k]The alkyl chloride, as its hydrochloride salt, used in place of the corresponding alkyl bromide, ws prepared as an oil of satisfactory purity from ethyl 1-methyl-pyrazole-4-carboxylate (Aust. J. Chem., 1983, 36, 135) using the method described in Chem. Abs., 1969, 71, 38813w of reduction with lithium aluminium hydride and chlorination with thionyl chloride.
[l]The alkyl mesylate, used in place of the corresponding alkyl bromide, was prepared as an oil of satisfactory purity, by the reaction of a mixture of 5-hydroxmethyl-1,2,3-thiadiazole [itself prepared by reduction of methyl 1,2,3-thiadiazole-5-carboxylate (GB Patent No. 2081265A) withlithium aluminium hydride], mesyl chloride and triethylaine in methylene chloride at 5° C.
[m]The alkyl chloride used in place of the corresponding alkyl bromide, was prepared as an oil of satisfactory purity frommethyl isothiazole-5-carboxylate [itself prepared by heating to reflux for 5 hours a mixture of isothiazole-5-carboxylic acid (J. Chem. Soc. 1964, 446), methanoland sulphuric acie] using the method described in note [k] immediately above.

EXAMPLES 213-219

A solution of diethyl azodicarboxylate (1.6 g) in chloroform (5 ml) was added dropwise to a mixture of 1,2-dihydro-1-carboethoxy-3H-indazol-3-one (1.5 g), triphenylphosphine (2 g) and trans-3-(3-pyridyl)-allyl alcohol [0.95 g; itself prepared from methyl trans-3-(3-pyridyl)-acrylate (J. Het. Chem., 1985, 22, 65) as an oil of satisfactory purity on reduction at 0° C. with a solution of di-isobutylaluminium hydride in toluene] in chloroform (20 ml). The mixture was stirred at ambient temperature for 16 hours and then evaporated to dryness. Diethyl ether was added, the mixture was filtered and the filtrate was evaporated The residue was chromatographed using an increasing gradient of ethyl acetate in petrol as eluant to give 1,2-dihydro-1-carboethoxy-2-[trans-3-(3-pyridyl)allyl]-3H-indazol-3-one (Ex. 213) as an oil (0.84 g) in 37% yield and of satisfactory purity as judged by NMR and mass spectral analysis.

Using a similar alkylation procedure, but employing the appropriate alcohol instead of the allyl alcohol used immediately above, there were obtained the following compounds of formula C (Ra=Rb=H; Rd=$CO_2Et$):

| Example | A | Q | m.p.* (°C.) | reaction duration (hours) | yield % |
|---|---|---|---|---|---|
| 214[a] | —CH$_2$— | 3-pyridazinyl | oil | 16 | 35 |
| 215[b] | —CH$_2$— | 3-methylpyrid-4-yl | oil | 24 | 22 |
| 216[c] | —CH$_2$— | 3-ethylpyrid-4-yl | oil | 24 | 32 |
| 217[d] | —CH$_2$— | 4-pyrimidinyl | 117–119 | 24 | 34 |
| 218[e] | —CH$_2$— | 4-methoxypyrid-3-yl | oil | 4 | 10 |
| 219[f] | —CH$_2$— | 3-methoxypyrid-4-yl | oil | 30 | 30 |

Notes
*Where the product was obtained as an oil it was shown to be of satisfactory purity as judged by TLC, IR and/or NMR analysis.
[a]3-Hydroxymethylpyriazine is described in Acta Chem. Scand., 1947, 1, 619.
[b]4-Hydroxymethyl-3-methylpyridine was prepared as a solid, m.p. 82–84° C. in 74% yield, by the reduction of ethyl 3-methylisonicotinate (J. Chem. Soc., 1984, 1501) with lithium aluminium hydride.
[c]3-Ethyl-4-hydroxymethylpyridine as described in J. Org. Chem. 1986, 51, 2289.
[d]4-Hydroxymethylpyridine is described in Bull. Soc. Chim. Belg., 1982, 91, 153.
[e]3-Hydroxymethyl-4-methoxypyridine was prepared as an oil of satisfactory purity by reduction of methyl 4-methoxynicotinate (prepared as described in J. Chem. Soc., 1966, 1819) withlithium aluminium hydride.
[f]4-Hydroxymethyl-3-methoxypyridine is described in Tet., 1958, 3, 60.

EXAMPLE 220

A mixture of 1,2-dihydro-2-(3-bromopyrid-5-ylmethyl)-1-carboethoxy-3H-indazol-3-one (2 g; Ex. 101), cuprous cyanide (0.75 g) and N,N-dimethylformamide (10 ml) was stirred and heated to 175° C. for 5 hours. The mixture was cooled, a saturated aqueous sodium bicarbonate solution was added and the mixture was extracted with methylene chloride (x3). The combined extracts were dried (MgSO$_4$) and evaporated to give 1,2-dihydro-1-ethoxy-2-(3-cyanopyrid-5-ylmethyl)-3H-indazol-3-one, as an oil (0.45 g) in 20% yield, of satisfactory purity as judged by IR and NMR analysis.

EXAMPLE 221

A mixture of 1,2-dihydro-2-(2-aminothiazol-4-ylmethyl)-1-carboethoxy-3H-indazol-3-one (3.2 g; Ex. 199) and acetic anhydride (10 ml) was heated to reflux for 1 hour. The mixture was evaporated to give 1,2-dihydro-2-(2-acetamidothiazol-4-ylmethyl)-1-carboethoxy-3H-indazol-3-one as a solid (2.8 g), m.p. 134–136° C. (recrystallised from ethyl acetate) in 76% yield.

EXAMPLE 222

The alkylation procedure described for the preparation of the starting material for Example 144 was repeated using 5-chloromethyl-1,2,4-triazole (J. Amer. Chem. Soc., 1955, 77, 1538) in place of trans-cinnamyl bromide and carrying out the reaction at ambient temperature. The product was purified by chromatography using a mixture of ethyl acetate and ethanol (50/1 v/v) as the eluant. There was thus obtained 1,2-dihydro-1-carboethoxy-2-(1,2,4-triazol-5-ylmethyl)-3H-indazol-3-one as a solid, m.p. 147–150° C. in 25% yield.

EXAMPLES 223–265

Using a similar hydrolysis procedure to that described in Examples 111–142, but using the appropriate 1,2-dihydro-1-carboethoxy-2-substituted-3H-indazol-3-one and carrying out the reaction at ambient temperature, there were obtained the following compounds of formula B (Ra=Rb=H):

| Example | A | Q | m.p. (°C.) | reaction duration (hours) | yield % |
|---|---|---|---|---|---|
| 223[a]* | —CH$_2$— | 3-cyanopyrid-5-yl | 217–219 | 0.5 | 30 |
| 224 | —CH$_2$— | 3-pyridazinyl | 151–153 | 0.3 | 75 |
| 225* | —CH$_2$— | 2-methylthiazol-5-yl | 183 | 0.8 | 68 |
| 226[b] | —CH$_2$— | 3-quinolyl | 213–215 | 0.8 | 61 |
| 227 | —CH$_2$— | 4-quinolyl | 194–200 | 0.8 | 76 |
| 228* | —CH$_2$— | 4-isoquinolyl | 249–251 | 0.3 | 89 |
| 229[c]* | —CH$_2$— | 3-pyridyl | 165 | 1 | 40 |
| 230 | —CH$_2$— | 4-thiazolyl | 147–149 | 0.5 | 42 |
| 231 | —CH$_2$— | 2-acetamidothiazol-4-yl | 250–260 | 0.5 | 75 |
| 232 | —CH$_2$— | 2-aminothiazol-4-yl | 220–222 | 0.5 | 59 |
| 233[d] | —CH$_2$— | 5-isoxazolyl | 125 | 0.5 | 32 |
| 234[d] | —CH$_2$— | 3,5-dimethylisoxazol-4-yl | 204 | 0.5 | 60 |
| 235 | —CH$_2$— | 3-pyrazolyl | 211–213 | 0.5 | 52 |
| 236 | —CH$_2$— | 4-pyrazolyl | 223–225 | 0.5 | 32 |
| 237 | —CH$_2$— | 1,2,3-triazol-4-yl | 158–160 | 0.3 | 82 |
| 238 | —CH$_2$— | 1,2,4-triazol-5-yl | 202–205 | 0.3 | 62 |
| 239 | —CH$_2$— | 1,2,5-thiadiazol-3-yl | 146–148 | 0.5 | 78 |
| 240 | —CH$_2$— | 1,2,3-thiadiazol-4-yl | 153–154 | 0.5 | 55 |
| 241[e] | —CH$_2$— | 3-indolyl | 194–198 | 3 | 55 |
| 242 | —CH$_2$— | 1,2-dihydro-3-oxo-3H-indazol-2-yl | 239–240 | 1 | 79 |
| 243 | —CH$_2$— | 4-methylpyrid-3-yl | 194–196 | 0.5 | 29 |
| 244[d] | —CH$_2$— | 3-chloropyrid-5-yl | 184–186 | 0.3 | 40 |
| 245[d] | —CH$_2$— | 3-fluoropyrid-5-yl | 195 | 1 | 36 |
| 246 | —CH$_2$— | 3-methylpyrid-4-yl | 180–181 | 0.5 | 64 |
| 247 | —CH$_2$— | 3-ethylpyrid-4-yl | 140–142 | 0.5 | 30 |
| 248 | —CH$_2$— | 2-methoxypyrid-4-yl | 179–180 | 0.5 | 56 |
| 249 | —CH$_2$— | 2-bromopyrid-4-yl | 160–161 | 0.5 | 50 |
| 250 | —CH$_2$— | 3-bromopyrid-4-yl | 186–187 | 0.5 | 40 |
| 251 | —CH$_2$— | 2-biphenylyl | 165–168 | 2 | 92 |
| 252 | —CH$_2$— | 2-pyridylthio | 120 | 0.3 | 85 |
| 253 | —CH$_2$— | phenoxy | 173–175 | 1 | 91 |
| 254[d] | —(CH$_2$)$_2$— | 3-pyridyl | 122 | 0.5 | 25 |
| 255 | —(CH$_2$)$_2$— | 4-pyridyl | 131–132 | 0.5 | 62 |
| 256[d] | —CH$_2$— | trans-(3-pyridyl)-vinyl | 173 | 0.5 | 23 |
| 257[f] | direct link | 2-propynyl | 170–174 | 0.3 | 88 |
| 258[g] | direct link | methylallyl | 182–185 | 0.5 | 88 |
| 259[d] | —CH$_2$— | 4-methoxypyrid-3-yl | 163 | 0.2 | 35 |
| 260[d] | —CH$_2$— | 3-methoxypyrid-4-yl | 156–158 | 0.5 | 55 |
| 261 | —CH$_2$— | 4-pyrimidinyl | 128–131 | 0.3 | 35 |
| 262[a] | —CH$_2$— | 1-methylimidazol-5-yl | 200 (decomp.) | 3 | 38 |
| 263[a] | —CH$_2$— | 1-methylpyrazol-4-yl | 166–168 | 1 | 76 |
| 264 | —CH$_2$— | 1,2,3-thiadiazol-5-yl | 160–162 | 0.5 | 35 |

-continued

| Example | A | Q | m.p. (°C.) | reaction duration (hours) | yield % |
|---|---|---|---|---|---|
| 265 | —CH$_2$— | 5-isothiazolyl | 142–143 | 0.3 | 55 |

Notes
*The reaction was carried out using the procedure described in Examples 111–142, that is the mixture was heated to reflux.
$^a$ Three equivalents of powdered potassium hydroxide were used.
$^b$ The hydrolysis was done at 50° C.
$^c$ Ex. 229, Ra = 7-methyl, Rb = H.
$^d$ Two equivalents of powdered potassium hydroxide were used.
$^e$ The starting material was 1,2-dihydro-2-[1-(t-butoxycarbonyl)indol-3-ylmethyl]-1-carboethoxy-3H-indazol-3-one (Ex. 205) and the hydrolysis was carried out at 40° C.
$^f$ The hydrolysis was carried out at 40° C.
$^g$ Ex. 258, Ra = 5-nitro, Rb = H.

EXAMPLE 266–269

Using a similar hydrolysis procedure to that described in Example 143, but employing the appropriate mixture of N- and O-alkylated compounds of formulae C and D respectively (Ra=Rb=H; Rd=CO$_2$Et) the following compounds of formula B (Ra=Rb=H) were obtained:

| Example | A | Q | m.p. (°C.) | reaction duration (hours) | yield % |
|---|---|---|---|---|---|
| 266$^a$ | —CH$_2$— | 4-imidazolyl | 222–229 | 1 | 77 |
| 267 | —CH$_2$— | 4-pyridazinyl | 171–172 | 1 | 13 |
| 268$^b$ | —CH$_2$— | cyclohexen-1-yl | 189–195 | 0.3 | 64 |
| 269$^c$ | —CH$_2$— | 3-pyridyl | 220–225 | 2 | 59 |

Notes
$^a$ The product is a mixture of the 4-imidazolyl and 5-imidazolyl tautomers.
$^b$ The hydrolysis was carried out using the conditions described in Example 111, that is a mixture of the N-and O-alkylated materials, potassium hydroxide and ethanol was heated to reflux.
$^c$ Ex. 269, Ra = 4-nitro, Rb = H; the hydrolysis was carried out using the conditions described in Example 111 except that the reaction was done at ambient temperature.

The necessary starting mixtures of N- and O-alkylated compounds of formulae C (Ra=Rb=H; Rd=CO$_2$Et) and D (Ra=Rb=H; Rd=CO$_2$Et) were obtained as follows:

A solution of diethyl azodicarboxylate (1.9 g) in tetrahydrofuran (12 ml) was added dropwise over 30 minutes to a mixture of t-butyl 4-hydroxymethylimidazole-1-carboxylate (1.4 g; itself prepared as an oil of satisfactory purity but in admixture with t-butyl 5-hydroxymethylimidazole-1-carboxylate by the reaction of 4-hydroxymethylimidazole and di-t-butyl dicarbonate using the process described in the portion of Ex. 154 which is concerned with the preparation of starting materials), triphenylphosphine (2.8 g) and 1,2-dihydro-1-carboethoxy-3H-indazol-3-one (1.5 g) in tetrahydrofuran (25 ml). The mixture was stirred at ambient temperature for 1.5 hours and then evaporated to dryness. Toluene was added, the mixture was filtered and the filtrate was evaporated. The residue was partitioned between ethyl acetate and M hydrochloric acid. The aqueous layer was separated, basified with sodium bicarbonate solution and extracted with ethyl acetate (x 3). The extracts were combined, dried (MgSO$_4$) and evaporated to leave an oil which crystallised on trituration in ethyl acetate. There was thus obtained 0.92 g (46%), m.p. 151° C., of a mixture of 1,2-dihydro-2-(1-t-butoxycarbonylimidazol-4-yl)methyl-1-carboethoxy-3H-indazol-3-one and 3-(1-t-butoxycarbonylimidazol-4-ylmethoxy)-1-carboethoxy-1H-indazole and the corresponding imidazol-5-yl derivatives (starting material for Ex. 266).

Using a similar alkylation procedure but employing 4-hydroxymethylpyridazine (prepared as described in *Monat. fur Chemie.*, 1973, 104, 1354) there was obtained, as an oil in 72% yield, a mixture of 1,2-dihydro-1-carboethoxy-2-(4-pyridazinyl)methyl-3H-indazol-3-one and 1-carboethoxy-3-(4-pyridazinyl)methoxy-1H-indazole (starting material for Ex. 267).

The alkylation procedure described in Example 109 was repeated except that the alkylating agent was cyclohex-1-enylmethyl bromide (*J. Chem. Soc.*, 1956, 4060) and the mixture was stirred at ambient temperature for 16 hours. There was thus obtained, as an oil in quantitative yield, a mixture of 1,2-dihydro-1-carboethoxy-2-(cyclohex-1-enyl)methyl-3H-indazol-3-one and 1-carboethoxy-3-(cyclohex-1-enyl)methoxy-1H-indazole (starting material for Ex. 268).

The alkylation procedure described in Example 108 was repeated except that 1,2-dihydro-1-carboethoxy-4-nitro-3H-indazol-3-one and 3-chloromethylpyridine hydrochloride were used as starting materials and the mixture was heated to reflux for 17 hours. There was thus obtained, as an oil in 56% yield, a mixture of 1,2-dihydro-1-carboethoxy-4-nitro-2-(pyrid-3-yl)methyl-3H-indazol-3-one and 1-carboethoxy-4-nitro-3-(pyrid-3-yl)methoxy-1H-indazole (starting material for Ex. 269).

1,2-Dihydro-1-carboethoxy-4-nitro-3H-indazol-3-one used immediately above was obtained from 2-amino-6-nitrobenzoic acid using the method described in *J. Med. Chem.*, 1984, 27, 768, except that stannous chloride was used instead of sodium sulphite to reduce the intermediate diazonium salt. The product so obtained was treated with ethyl chloroformate in the presence of a mixture of 4-dimethylaminopyridine and pyridine (1/9 v/v) at ambient temperature for 15 hours. There was thus obtained as a solid, m.p. 234–236° C., 1,2-dihydro-1-carboethoxy-4-nitro-3H-indazol-3-one.

EXAMPLE 270

Using an analogous procedure to that described in Examples 48–51 treatment of 1,2-dihydro-2-benzyl-6-methoxy-3H-indazol-3-one (Ex. 174) with boron tribromide gave 1,2-dihydro-2-benzyl-6-hydroxy-3H-indazol-3-one as a solid, m.p. 206–207° C. in 21% yield.

EXAMPLES 271–272

1,2-Dihydro-2-(2-diacetylaminobenzyl)-3H-indazol-3-one (Ex. 152) was obtained as the second component of a three component mixture formed on acetylation of 1,2-dihydro-2-(2-aminobenzyl)-3H-indazol-3-one (Ex. 151). Further elution of the chromatography column gave the third component which proved to be 1,2-dihydro-2-(2-acetamidobenzyl)-1-acetyl-3H-indazol-3-one (Ex. 271), obtained as a solid (0.2 g), m.p. 171–173° C. in 31% yield.

Using a similar hydrolysis procedure to that described in Examples 111–142, but using the 1-acetyl-3H-indazol-3-one (Ex. 271) as starting material and carrying out the reaction at ambient temperature for 5 minutes there was obtained a crude product which was purified by chromatography using a mixture of methylene chloride/ether/methanol (10/10/1 v/v) as eluant. There was thus obtained 1,2-dihydro-2-(2-acetamidobenzyl)-3H-indazol-3-one (Ex. 272) as a solid, m.p. 238–243° C. in 83% yield.

EXAMPLE 273

A mixture of 1,2-dihydro-6-amino-2-(3-pyridylmethyl)-3H-indazol-3-one (1.8 g), bis(trimethylsilyl)acetamide (2.5 ml) and chloroform was stirred at ambient temperature for 30 minutes. Triethylamine (2.1 ml) and hexanoic acid anhydride (2.9 ml) were added in turn and the mixture was heated to reflux for 2 hours. The mixture was evaporated, the residue was dissolved in methanol (20 ml), 2M sodium hydroxide (10 ml) was added and the mixture was heated to 40° C. for 30 minutes. The mixture was cooled, acidified to pH 6 with M hydrochloric acid and the bulk of the methanol was evaporated. The residue was extracted with ethyl acetate (x4). The combined extracts were dried (MgSO$_4$) and evaporated. The residue was purified by chromatography using a mixture of methylene chloride and methanol (95/5 v/v) as eluant. There was thus obtained 1,2-dihydro-6-hexanamido-2-(3-pyridylmethyl)-3H-indazol-3-one as a solid (0.85 g), m.p. 173–174° C. in 50% yield.

The 1,2-dihydro-6-amino-2-(3-pyridylmethyl)-3H-indazol-3-one used as starting material was obtained as follows:

A similar procedure to that described in Example 1 was repeated but starting from 4-carbomethoxy-2-nitro-N-(3-pyridylmethyl)-benzamide [itself prepared as a solid, m.p. 96–100° C. in 92% yield, from 4-carbomethoxy-2-nitrobenzoyl chloride (prepared by the reaction of 4-carbomethoxy-2-nitrobenzoic acid (Beilstein, 9, 852) and thionyl chloride) and 3-aminomethylpyridine using the process described for the preparation of the starting material for Ex. 24], using 2M sodium hydroxide (2 equivalents) as the base, using ethanol in place of methanol as the reaction solvent and having a reaction duration of 3 hours. There was thus obtained 1,2-dihydro-6-carboxy-2-(3-pyridylmethyl)-3H-indazol-3-one as a solid, m.p. 275–280° C. in 82% yield.

The product so obtained (4.84 g) was suspended in N,N-dimethylformamide (25 ml). Diphenylphosphoryl azide (4.65 ml) and then t-butanol (6.8 ml) were added in turn followed by the dropwise addition of triethylamine (3.25 ml). The mixture was stirred at ambient temperature for 1 hour, then heated to 80° C. for 3 hours. The solvent was evaporated and the residue was purified by chromatography using a mixture of methylene chloride and methanol (95/5 v/v) as eluant. There was thus obtained 1,2-dihydro-6-t-butoxycarbonylamino-2-(3-pyridylmethyl)-3H-indazol-3-one as a solid (3.7 g) m.p. 185–205° C. (decomp.) in 61% yield.

A mixture of the product so obtained, trifluoroacetic acid (20 ml) and methylene chloride (20 ml) was stirred at ambient temperature for 2 hours and evaporated. Diethyl ether was added to the residue and the product was filtered off. There was thus obtained 1,2-dihydro-6-amino-2-(3-pyridylmethyl)-3H-indazol-3-one (starting material for Ex. 273) as a solid (1.8 g), m.p. 150° C. in 70% yield.

EXAMPLE 274

The following illustrate representative pharmaceutical dosage forms containing the compound of formula I, or a (1-4C)alkoxycarbonyl derivative thereof, or a salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 mg |
| Lactose Ph.Eur | 488.5 |
| Magnesium stearate | 1.5 |

| (e) Injection I | (50 mg/ml) |
|---|---|
| Compound X | 5.0% w/v |
| 1 M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate EP | 3.6% w/v |
| 0.1 M Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |

-continued

| Dichlorotetrafluoroethane | 191.6 |

Note
The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

Chemical Formulae

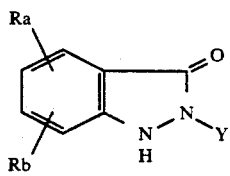
I

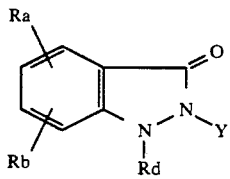
II

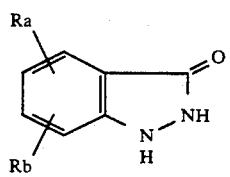
III

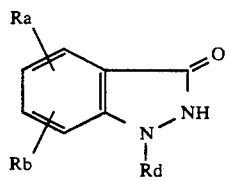
IV

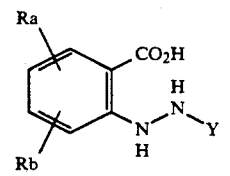
V

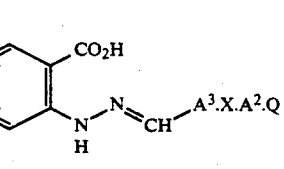
VIa

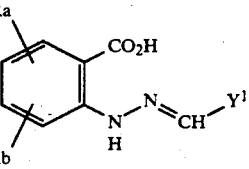
VIb

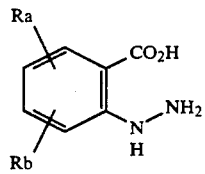
VII

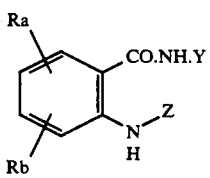
VIII

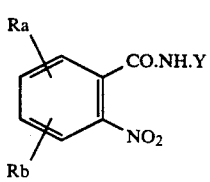
IX

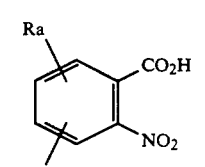
X

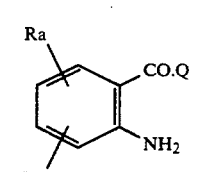
XII

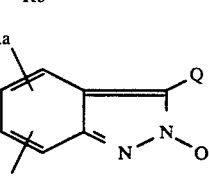
XI

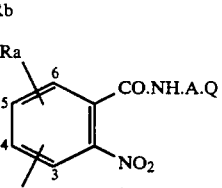
A

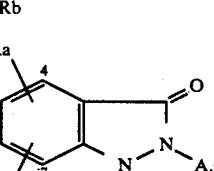
B

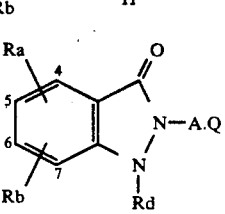
C

Chemical Formulae

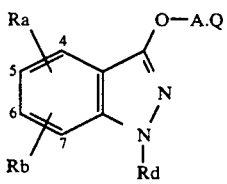

D

What is claimed includes the following:

1. A pharmaceutical composition comprising as active ingredient a 1,2-dihydro-3H-indazol-3-one of the formula I in a 5-lipoxygenase inhibitory amount

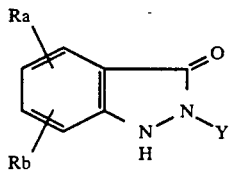

I wherein Ra is hydrogen, halogeno, nitro, hydroxy, (2-6C)alkanoyloxy, (1-6C)alkyl, (1-6C)alkoxy, fluoro-(1-4C)alkyl, (2-6C)alkanoyl, amino, (1-6C)alkylamino, di-[(1-4C)-alkyl]amino, (2-6C)alkanoylamino or hydroxy-(1-6C)alkyl; Rb is hydrogen, halogeno, (1-6C)alkyl or (1-6C)alkoxy; and Y is a group of the formula —A¹—X—A²—Q in which A¹ is (1-6C)alkylene, (3-6C)alkenylene, (3-6C)alkynylene or cyclo(3-6C)alkylene optionally bearing a substituent selected from hydroxy, cyano, carbamoyl, carboxy, (1-4C)alkoxycarbonyl and phenyl, or A¹ is phenylene optionally bearing a substituent selected from halogeno, trifluoromethyl, (1-6C)alkyl or (1-6C)alkoxy; X is oxy, thio, sulphinyl, sulphonyl, imino, (1-6C)alkylimino, (1-6C)-alkanoylimino, iminocarbonyl (that is —NH.CO— or —CO.NH—) or phenylene optionally bearing a substituent selected from halogeno, trifluoromethyl, (1-6C)alkyl or (1-6C)alkoxy, or X is a direct link to A²; A² is (1-6C)alkylene, (3-6C)alkenylene or (3-6C)alkynylene in which one constituent methylene group may be replaced by an oxy or thio group, or A² is cyclo (3-6C)alkylene as defined above or is a direct link to Q; or Y is (2-10C)alkyl, (3-10C)alkenyl or (3-6C)alkynyl optionally bearing a substituent selected from (1-6C)alkoxy, (1-6C)alkylthio, (1-6C)alkylsulphinyl, (1-6C)alkylsulphonyl, cyano, carbamoyl, N-[(1-6C)alkyl]carbamoyl, N,N-di-[(1-4C)alkyl]carbamoyl, amino, (1-6C)alkylamino, di-[(1-4C)alkyl]amino, morpholino, piperidino, thiophenoxy and phenoxy; and Q is heteroaryl or a hydrogenated derivative thereof, which may optionally bear one or two substituents selected from (1-10C)alkyl, (2-10C)alkenyl, (1-10C)alkoxy, halogeno, nitro, hydroxy, oxo, (1-6C)alkylthio, (1-6C)alkylsulphinyl, (1-6C)alkylsulphonyl, amino, (1-6C)alkylamino, di-[(1-4C)alkyl]amino, carbamoyl, N-[(1-6C)alkyl]carbamoyl, N,N-di-[(1-4C)alkyl]carbamoyl, cyano, (1-4C)alkoxycarbonyl, carboxy, phenyl, phenyl-(1-4C)alkyl, fluoro-(1-4C)alkyl, (2-6C)alkanoyl, (2-6C)alkanoylamino, di-[(2-6C)alkanoyl]amino and hydroxy-(1-6C)alkyl, or may bear a (1-4C)alkylenedioxy substituent; and wherein any one or more of said phenyl, phenoxy or thiophenoxy substituents may themselves optionally bear one or two optional substituents selected from halogeno, fluoro-(1-4C)alkyl, nitro, carbamoyl, N-[(1-6C)alkyl]-carbamoyl, N,N-di[(1-4C)alkyl]carbamoyl, cyano, (1-6C)alkyl and (1-6C)alkoxy substituents; provided that when Y is butyl, Ra is other than hydrogen, chloro, methyl or ethyl; and when Y is a straight chain (2-5C)alkyl optionally bearing a terminally situated hydroxy substituent, Ra is other than hydrogen;

or a pharmaceutically acceptable salt thereof; or a (1-4C)alkoxycarbonyl derivative thereof; said active ingredient together with a pharmaceutically acceptable diluent or carrier.

2. A pharmaceutical composition as claimed in claim 1 wherein the active ingredient is a 1,2-dihydro-3H-indazol-3-one of the formula I in which Ra and Rb have the meanings defined in claim 1; and Y is a group of the formula —A¹—X—A²—Q in which A¹ is (1-6C)alkylene, (3-6C)alkenylene, (3-6C)alkynylene or cyclo(3-6C)alkylene optionally bearing a substituent selected from hydroxy, cyano, carbamoyl, carboxy, (1-4C)alkoxycarbonyl and phenyl or A¹ is phenylene optionally bearing a substituent selected from halogeno, trifluoromethyl, (1-6C)alkyl or (1-6C)alkoxy; X is oxy, thio, sulphinyl, sulphonyl, imino, (1-6C)alkylimino, (1-6C)-alkanoylimino, iminocarbonyl (that is —NH.CO— or —CO.NH—) or phenylene optionally bearing a substituent selected from halogeno, trifluoromethyl, (1-6C)alkyl or (1-6C)alkoxy, or X is a direct link to A², A² is (1-6C)alkylene, (3-6C)alkenylene or (3-6C)alkynylene in which one constituent methylene group may be replaced by an oxy or thio group, or A² is cyclo(3-6C)alkylene as defined above or is a direct link to Q; or Y is (2-10C)alkyl or (3-10C)alkenyl optionally bearing a substituent selected from (1-6C)alkoxy, (1-6C)alkylthio, (1-6C)alkylsulphinyl, (1-6C)alkylsulphonyl, cyano, carbamoyl, N-[(1-6C)alkyl]carbamoyl, N,N-di-[(1-4C)alkyl]carbamoyl, amino, (1-6C)alkylamino, di-[(1-4C)alkyl]amino, morpholino, piperidino, thiophenoxy and phenoxy; and Q is heteroaryl or a hydrogenated derivative thereof, which may optionally bear one or two substituents selected from (1-10C)alkyl, (2-10C)alkenyl, (1-10C)alkoxy, halogeno, nitro, hydroxy, (1-6C)alkylthio, (1-6C)alkylsulphinyl, (1-6C)alkylsulphonyl, amino, (1-6C)alkylamino, di-[(1-4C)alkyl]amino, carbamoyl, N-[(1-6C)alkyl]carbamoyl, N,N-di-[(1-4C)carbamoyl, cyano, (1-4C)alkoxycarbonyl, carboxy, phenyl, phenyl-(1-4C)alkyl, fluoro-(1-4C)alkyl, (2-6C)alkanoyl, (2-6C)alkanoylamino, di-[(2-6C)alkanoyl]amino and hydroxy-(1-6C)alkyl, or may bear a (1-4C)alkylenedioxy substituent; and wherein any one or more of said phenyl, phenoxy or thiophenoxy substituents may themselves optionally bear one or two optional substituents selected from halogeno, fluoro-(1-4C)alkyl, nitro, carbamoyl, N-[(1-6C)alkyl]carbamoyl, N,N-di[(1-4C)alkyl]carbamoyl, cyano, (1-6C)alkyl and (1-6C)alkoxy substituents; and subject to the provisos stated in claim 1; or a pharmaceutically acceptable salt thereof; or a (1-4C)alkoxycarbonyl derivative thereof.

3. A pharmaceutical composition as claimed in claim 1 wherein the active ingredient is a 1,2-dihydro-3H-indazol-3-one of the formula I which Ra and Rb have the meanings defined in claim 1; and Y is a group of the formula —A¹—X—A²—Q in which A¹ is (1-6C)alkylene, (3-6C)alkenylene, (3-6C)alkynylene or cyclo(3-6C)alkylene optionally bearing a substituent selected from hydroxy, cyano, carbamoyl, carboxy, (1-4C)alkoxycarbonyl and phenyl; X is oxy, thio, sulphinyl, sulphonyl, iminocarbonyl (that is —NH.CO— or —CO.NH—) or phenylene optionally bearing a substituent selected from halogeno, trifluoromethyl, (1-6C)alkyl or (1-6C)alkoxy, or X is a direct link to $A^2$, $A^2$ is (1-6C)alkylene, (3-6C)alkenylene or (3-6C)alkynylene in which one constituent methylene group may be replaced by an oxy or thio group, or $A^2$ is cyclo(3-6C)alkylene as defined above or is a direct link to Q; or Y is (2-10C)alkyl or (3-10C)alkenyl optionally bearing a substituent selected from (1-6C)alkoxy, (1-6C)alkylthio, (1-6C)alkylsulphinyl, (1-6C)alkylsulphonyl, carbamoyl, N-[(1-6C)alkyl]carbamoyl, N,N-di-[(1-4C)alkyl]carbamoyl, thiophenoxy and phenoxy; and Q is heteroaryl or a hydrogenated derivative thereof, which may optionally bear one or two substituents selected from (1-10C)alkyl, (2-10C)alkenyl, (1-10C)alkoxy, halogeno, nitro, hydroxy, (1-6C)alkylthio, (1-6C)alkylsulphinyl, (1-6C)alkylsulphonyl, carbamoyl, N-[(1-6C)alkyl]carbamoyl, N,N-di-[(1-4C)alkyl]carbamoyl, cyano, (1-4C)alkoxycarbonyl, carboxy, fluoro-(1-4C)alkyl, (2-6C)alkanoyl, (2-6C)alkanoylamino and hydroxy-(1-6C)alkyl, or may bear a (1-4C)alkylenedioxy substituent; and wherein any one or more of said phenyl, phenoxy or thiophenoxy substituents may themselves optionally bear one or two optional substituents selected from halogeno, fluoro-(1-4C)alkyl, nitro, cyano, (1-6C)alkyl and (1-6C)alkoxy substituents; and subject to the provisos stating in claim 1; or a pharmaceutically acceptable salt thereof; or a (1-4C)alkoxycarbonyl derivative thereof.

4. A pharmaceutical composition as claimed in claim 1 wherein the active ingredient is a 1,2-dihydro-3H-indazol-3-one of the formula I in which Ra is hydrogen, fluro, chloro, bromo, iodo, nitro, hydroxy, acetoxy, propionyloxy, butyryloxy, methyl, ethyl, propyl, isopropyl, butyl, methoxy, ethoxy, propoxy, isopropoxy, butoxy, trifluoromethyl, 2,2,2-trifluoroethyl, pentafluoroethyl, acetyl, propionyl, butyryl, hexanoyl, amino, methylamino, ethylamino, propylamino, butylamino, pentylamino, hexylamino, dimethylamino, diethylamino, dipropylamino, acetamido, propionamido, butyramido, hexanamido, hydroxymethyl, 2-hydroxyethyl, 1-hydroxyethyl or 3-hydroxypropyl;

Rb is hydrogen, fluoro, chloro, bromo, iodo, methyl, ethyl, propyl, isopropyl, butyl, methoxy, ethoxy, propoxy, isopropoxy or butoxy; and Y is a group of the formula —$A^1$—X—$A^2$—Q in which $A^1$ is methylene, ethylene, ethylidene, trimethylene, propylidene, tetramethylene, pentamethylene, 1-propenylene, 2-propenylene, 1-butenylene, 2-butenylene, 3-butenylene, 2-propynylene, 2-butynylene, 3-butynylene, cyclopropylidene, 1,2-cyclopropylene, cyclopentylidene, 1,2-cyclopentylene, 1,3-cyclopentylene, cyclohexylidene or 1,4-cyclohexylene optionally bearing a substituent selected from hydroxy, cyano, carbamoyl, carboxy, methoxycarbonyl, ethoxycarbonyl, t-butoxycarbonyl and phenyl or $A^1$ is phenylene optionally bearing a substituent selected from fluoro, chloro, bromo, trifluoromethyl, methyl, ethyl, propyl, methoxy, ethoxy, propoxy or isopropoxy;

X is oxy, thio, sulphinyl, sulphonyl, imino, methylimino, ethylimino, propylimino, hexylimino, acetylimino, propionylimino, butyrylimino, iminocarbonyl or phenylene optionally bearing a substituent selected from fluoro, chloro, bromo, trifluoromethyl, methyl, ethyl, propyl, methoxy, ethoxy, propoxy or isopropoxy, or X is a direct link to $A^2$; $A^2$ is methylene, ethylene, ethylidene, trimethylene, propylidene, tetramethylene, pentamethylene, 1-propenylene, 2-propenylene, 1-butenylene, 2-butenylene, 3-butenylene, 2-propynylene, 2-butynylene or 3-butynylene in which one constituent methylene group may be replaced by an oxy or thio group, or $A^2$ is cyclopropylidene, 1,2-cyclopropylene, cyclopentylidene, 1,2-cyclopentylene, 1,3-cyclopentylene, cyclohexylidene or 1,4-cyclohexylene optionally bearing a substituent selected from hydroxy, cyano, carbamoyl, carboxy, methoxycarbonyl, ethoxycarbonyl, t-butoxycarbonyl and phenyl or $A^2$ is a direct link to Q; or Y is ethyl, propyl, butyl, pentyl, neopentyl, hexyl, octyl, allyl, allenyl, 2-methyl-2-propenyl, 3,5-hexadienyl, 2-propynyl, 2-butynyl or 3-butynyl optionally bearing a substituent selected from methoxy, ethoxy, propoxy, isopropoxy, butoxy, hexyloxy, methylthio, ethylthio, propylthio, methylsulphinyl, ethylsulphinyl, propylsulphinyl, methylsulphonyl, ethylsulphonyl, propylsulphonyl, cyano, carbamoyl, N-methylcarbamoyl, N-ethylcarbamoyl, N-butylcarbamoyl, N,N-dimethylcarbamoyl, N,N-diethylcarbamoyl, amino, methylamino, ethylamino, butylamino, dimethylamino, diethylamino, morpholino, piperidino, thiophenoxy and phenoxy;

and Q is furyl, benzofuranyl, tetrahydrofuryl, chromanyl, thienyl, pyridyl, quinolyl, isoquinolyl, pyrazinyl, pyrimidinyl, pyridazinyl, pyrrolyl, indolyl, imidazolyl, N-methylimidazolyl, benzimidazolyl, pyrazolyl, indazolyl, oxazolyl, isoxazolyl, thiazolyl, isothiazolyl, 1,2,3-trazolyl, 1,2,4-trazolyl, oxadiazolyl, furazanyl or thiazdiazolyl, which may optionally bear one or two substituents selected from methyl, ethyl, propyl, butyl, hexyl, octyl, vinyl, 1-propenyl, allyl, 2-methyl-2-propenyl, 3,5-hexadienyl, methoxy, ethoxy, propoxy, isopropoxy, butoxy, 1-methylhexyloxy, nonyloxy, fluoro, chloro, bromo, nitro, hydroxy, oxo, methylthio, ethylthio, butylthio, methylsulphinyl, ethylsulphinyl, butylsulphinyl, methylsulphonyl, ethylsulphonyl, butylsulphonyl, amino, methylamino, ethylamino, propylamino, butylamino, pentylamino, hexylamino, dimethylamino, diethylamino, dipropylamino, carbamoyl, N-methylcarbamoyl, N-ethylcarbamoyl, N-propylcarbamoyl, N,N-dimethylcarbamoyl, N,N-diethylcarbamoyl, cyano, methoxycarbonyl, ethoxycarbonyl, t-butoxycarbonyl, carboxy, phenyl, benzyl, phenethyl, phenylpropyl, phenylbutyl, trifluoromethyl, pentafluoroethyl, acetyl, propionyl, butyryl, hexanoyl, acetamido, propionamido, butyramido, diacetylamino, dipropionylamino, hydroxymethyl, 1-hydroxyethyl, 2-hydroxyethyl, 1-hydroxypropyl, 1-hydroxypentyl and 1-hydroxyhexyl, or Q may bear a methylenedioxy or ethylenedioxy substituent; and wherein any one or more of said phenyl, phenoxy or thiophenoxy substituents may themselves optionally bear one or two optional substituents selected from fluoro, chloro, bromo, iodo, trifluoromethyl, 2,2,2-trifluoroethyl, pentafluoroethyl, nitro, carbamoyl, N-methylcarbamoyl, N-ethylcarbamoyl, N-propylcarbamoyl, N,N-dimethylcarbamoyl, N,N-diethylcarbamoyl, cyano, methyl, ethyl, propyl, isopropyl, butyl, methoxy, ethoxy, propoxy, isopropoxy and butoxy;

provided that when Y is butyl, Ra is other than hydrogen, chloro, methyl or ethyl; and when Y is ethyl, propyl, butyl or pentyl optionally bearing a terminally situated hydroxy substituent, Ra is other than hydrogen; or a pharmaceutically acceptable salt thereof; or a methoxycarbonyl, ethoxycarbonyl or t-butoxycarbonyl derivative thereof.

5. A pharmaceutical composition as claimed in claim 1 wherein the active ingredient is a 1,2-dihydro-3H-indazol-3-one of the formula I in which Ra is hydrogen, fluoro, chloro, bromo, nitro, hydroxy, acetoxy, methyl, ethyl, propyl, isopropyl, methoxy, ethoxy, propoxy, isopropoxy, butoxy, acetamido, propionamido, butyramido or hexanamido; Rb is hydrogen, methoxy, ethoxy, propoxy or isopropoxy; and Y is a group of the formula —$A^1$—X—$A^2$—Q in which $A^1$ is methylene, ethylene, ethylidene, trimethylene, propylidene, tetramethylene, pentamethylene, 2-propenylene, 2-butenylene, 2-propynylene, 2-butynylene, cyclopropylidene, 1,2-cyclopropylene, cyclopentylidene or 1,2-cyclopentylene optionally bearing a phenyl substituent or $A^1$ is phenylene; X is oxy, thio, sulphinyl, sulphonyl, imino, methylimino or acetylimino, or X is a direct link to $A^2$; $A^2$ is methylene, ethylene, ethylidene, cyclopropylidene or 1,2-cyclopropylene or $A^2$ is a direct link to Q; or Y is ethyl, propyl, butyl, neopentyl, hexyl, octyl, allyl, allenyl, 2-methyl-2-propenyl, 2-propynyl or 2-butynyl optionally bearing a substituent selected from amino, methylamino, ethylamino, dimethylamino, diethylamino, morpholino and piperidino;

and Q is indenyl, indanyl, furyl, benzofuranyl, tetrahydrofuryl, chromanyl, thienyl, pyridyl, quinolyl, isoquinolyl, pyrazinyl, pyrimidinyl, pyridazinyl, pyrrolyl, indolyl, imidazolyl, N-methylimidazolyl, benzimidazolyl, pyrazolyl, indazolyl, oxazolyl, isoxazolyl, thiazolyl, isothiazolyl, 1,2,3-triazolyl, 1,2,4-triazolyl, oxadiazolyl, furazanyl or thiadiazolyl, which may optionally bear one or two substituents selected from methyl, ethyl, propyl, butyl, allyl, methoxy, ethoxy, propoxy, isopropoxy, butoxy, 1-methylhexyloxy, nonyloxy, fluoro, chloro, bromo, nitro, hydroxy, oxo, methylthio, ethylthio, butylthio, methylsulphinyl, ethylsulphinyl, butylsulphinyl, methylsulphonyl, ethylsulphonyl, butylsulphonyl, amino, methylamino, ethylamino, dimethylamino, diethylamino, cyano, methoxycarbonyl, ethoxycarbonyl, t-butoxycarbonyl, phenyl, benzyl, phenethyl, phenylpropyl, trifluoromethyl, acetamido, propionamido, butyramido, diacetylamino, hydroxymethyl, 1-hydroxyethyl, 2-hydroxyethyl, 1-hydroxypropyl, 1-hydroxypentyl and 1-hydroxyhexyl, or Q may bear a methylenedioxy or ethylenedioxy substituent; and wherein any one of said phenyl, substituents may optionally bear one or two optional substituents selected from fluoro, chloro and bromo; provided that when Y is butyl, Ra is other than hydrogen, chloro, methyl or ethyl; and when Y is ethyl, propyl, butyl or pentyl optionally bearing a terminally situated hydroxy substituent, Ra is other than hydrogen; or a pharmaceutically acceptable salt thereof.

6. A method of treating a disease or medical condition mediated alone or in part by one or more leukotrienes which comprises administering to a warm-blooded animal requiring such treatment an effective amount of a 1,2-dihydro-3H-indazolone of the formula I wherein Ra, Rb and Y have the meanings defined in claim 1 or a pharmaceutically acceptable salt thereof; or a (1-4C)alkoxycarbonyl derivative thereof; or of a 1,2-dihydro-3H-indazolone of formula I wherein Y is butyl, Ra is hydrogen, halogeno, methyl or ethyl and Rb is hydrogen; or wherein Y is a straight chain (2-5C)alkyl optionally bearing a terminally situated hydroxy substituent, and Ra and Rb are hydrogen; or a pharmaceutically acceptable salt thereof, or a (1-4C)alkoxycarbonyl derivative thereof.

7. A pharmaceutical composition which comprises a compound of the formula I as defined in claim 6, or a pharmaceutically acceptable salt thereof, or a (1-4C)alkoxycarbonyl derivative thereof, in conjunction or admixture with a cyclooxygenase inhibitory non-steroidal anti-inflammatory agent and a pharmaceutically acceptable diluent or carrier.

* * * * *